(12) United States Patent
Sragow et al.

(10) Patent No.: US 11,515,018 B2
(45) Date of Patent: Nov. 29, 2022

(54) SYSTEMS AND METHODS FOR PATIENT RECORD MATCHING

(71) Applicant: Express Scripts Strategic Development, Inc., St. Louis, MO (US)

(72) Inventors: Howard M. Sragow, West Orange, NJ (US); Elisa D. Kreitzman, Cherry Hill, NJ (US); Steven V. Russo, North Caldwell, NJ (US); Mateen Ahmad, Iselin, NJ (US)

(73) Assignee: Express Scripts StrategiC Development, Inc., St. Louis, MO (US)

( * ) Notice: Subject to any disclaimer, the term of this patent is extended or adjusted under 35 U.S.C. 154(b) by 0 days.

(21) Appl. No.: 17/682,352

(22) Filed: Feb. 28, 2022

(65) Prior Publication Data

US 2022/0180988 A1   Jun. 9, 2022

Related U.S. Application Data

(63) Continuation-in-part of application No. 17/365,142, filed on Jul. 1, 2021, which is a continuation-in-part
(Continued)

(51) Int. Cl.
*G16H 10/60* (2018.01)
*G06N 20/00* (2019.01)

(52) U.S. Cl.
CPC ............. *G16H 10/60* (2018.01); *G06N 20/00* (2019.01)

(58) Field of Classification Search
CPC ............................... G16H 10/60; G06N 20/00
See application file for complete search history.

(56) References Cited

U.S. PATENT DOCUMENTS

| 7,725,479 B2 | 5/2010 | Cornacchia, III |
| 8,571,885 B2 | 10/2013 | Andros |

(Continued)

OTHER PUBLICATIONS

Navarro, "A Guided Tour to Approximate String Matching" ACM Computing Surveys, vol. 33, No. 1, Mar. 2001, pp. 31-88 (58 pages).

(Continued)

*Primary Examiner* — Robert A Sorey
*Assistant Examiner* — Kimberly A. Sass
(74) *Attorney, Agent, or Firm* — The Small Patent Law Group

(57) ABSTRACT

An AI record matching system includes processors that may compare patient records using one or more rules, criteria, or parameters and determine whether any of the patient records include different demographic information but include same medical information for a same person based on comparing the patient records using the one or more rules, criteria, or parameters. The processors may receive feedback data indicating an overmatching of the patient records to the same person or an undermatching of the patient records to the same person. The processors may be trained by modifying the one or more rules, criteria, or parameters based on the feedback data. The processors may iteratively repeat one or more of examining the patient records, determining whether any of the patient records include the different demographic information but the same medical information for the same person, receiving the feedback data, and training the one or more processors.

20 Claims, 14 Drawing Sheets

Related U.S. Application Data of application No. 17/174,743, filed on Feb. 12, 2021, which is a continuation-in-part of application No. 16/998,509, filed on Aug. 20, 2020, which is a continuation-in-part of application No. 16/184,957, filed on Nov. 8, 2018, now abandoned.

(56) References Cited

U.S. PATENT DOCUMENTS

| | | | |
|---|---|---|---|
| 8,762,176 | B2 | 6/2014 | Banfield |
| 9,129,046 | B2 * | 9/2015 | Bess ............... G06F 16/245 |
| 9,406,072 | B2 | 8/2016 | Whitman |
| 9,547,679 | B2 | 1/2017 | Whitman |
| 9,734,288 | B2 | 8/2017 | Pecora |
| 9,734,289 | B2 | 8/2017 | Pecora |
| 9,892,231 | B2 | 2/2018 | Vdovjak |
| 10,275,828 | B2 | 4/2019 | Reisz |
| 10,290,039 | B2 | 5/2019 | Hueter |
| 10,340,033 | B2 * | 7/2019 | Bucur ............... G06Q 10/06 |
| 10,558,785 | B2 | 2/2020 | Cox |
| 10,600,088 | B2 | 3/2020 | Dittus |
| 10,657,613 | B2 | 5/2020 | Bucur |
| 10,707,982 | B2 | 7/2020 | Gibson |
| 10,825,093 | B2 | 11/2020 | Joseph |
| 10,878,962 | B2 | 12/2020 | Smith |
| 2005/0256742 | A1 | 11/2005 | Kohan |
| 2007/0038471 | A1 | 2/2007 | Meisel |
| 2007/0073582 | A1 | 3/2007 | Jung |
| 2007/0156509 | A1 | 7/2007 | Jung |
| 2007/0203828 | A1 | 8/2007 | Jung |
| 2011/0193797 | A1 * | 8/2011 | Unruh ............... G06F 3/0233 345/173 |
| 2011/0246238 | A1 | 10/2011 | Vdovjak |
| 2012/0173285 | A1 * | 7/2012 | Muthukrishnan ...... G06Q 10/10 705/2 |
| 2013/0197935 | A1 | 8/2013 | Obst |
| 2013/0262141 | A1 * | 10/2013 | Crockett ............... G16H 50/20 705/3 |
| 2014/0052469 | A1 | 2/2014 | Andros |
| 2014/0324523 | A1 | 10/2014 | Ray |
| 2014/0324524 | A1 | 10/2014 | Ray |
| 2015/0058034 | A1 | 2/2015 | Ayshford |
| 2015/0066540 | A1 | 3/2015 | Wason |
| 2015/0106123 | A1 | 4/2015 | Amarasingham |
| 2015/0278452 | A1 * | 10/2015 | Neff ............... G16Z 99/00 705/3 |
| 2016/0071017 | A1 * | 3/2016 | Adjaoute ............... G06Q 20/4016 706/52 |
| 2016/0098748 | A1 | 4/2016 | Dittus |
| 2016/0105699 | A1 | 4/2016 | Luzzi |
| 2016/0188734 | A1 | 6/2016 | Morley |
| 2016/0210427 | A1 | 7/2016 | Mynhier |
| 2016/0292456 | A1 | 10/2016 | Dubey |
| 2016/0335674 | A1 | 11/2016 | Plourde |
| 2016/0342999 | A1 | 11/2016 | Routson |
| 2017/0213127 | A1 | 7/2017 | Duncan |
| 2018/0322946 | A1 | 11/2018 | Ika |
| 2019/0279242 | A1 | 9/2019 | Welch, Jr. |
| 2020/0013496 | A1 | 1/2020 | Vandervoort |

OTHER PUBLICATIONS

The Sequoia Project, "A Framework for Cross-Organizational Patient Identify Management", 2018.

* cited by examiner

SYSTEMS AND METHODS FOR PATIENT RECORD MATCHING

CROSS-REFERENCE TO RELATED APPLICATIONS

This application is a continuation-in-part of U.S. patent application Ser. No. 17/365,142 (filed 1 Jul. 2021), which is a continuation-in-part of U.S. patent application Ser. No. 17/174,743 (filed 12 Feb. 2021), which is a continuation-in-part of U.S. patent application Ser. No. 16/998,509 (filed 20 Aug. 2020), which is a continuation-in-part of U.S. patent application Ser. No. 16/184,957 (filed 8 Nov. 2018). The entire disclosures of these applications are incorporated herein by reference.

BACKGROUND

Health care is provided to patients using health care records that are associated with patients throughout their lives. Information can be included in these records to try and associate each record with a different patient. In the United States, however, there is no unique identifier assigned to each patient to ensure that each health care record is correctly associated with the same patient. Each health care provider, processor, and payor make individual decisions about for whom each service is being performed, and whether the patient receiving the service is the same as another patient who received another service on a different day. With millions of providers; thousands of insurers; patients constantly moving between providers and insurers; and a constant stream of demographic volatility and typographical errors, it can be very difficult to confidently decide who is who and which record represents the health care provided to which patient.

Patient-matching processes attempt to determine whether two or more patient health care records are associated with the same patient. For example, these processes attempt to determine whether patient records from the same or different health care provider, processor, and/or payor represent health care received by the same person. These processes try to avoid overmatching the records, which occurs when multiple records are determined to belong to (e.g., are associated with) the same person when the records belong to different people. These processes also try to avoid undermatching, which occurs when multiple records are determined to belong to two different people when the records belong to the same person.

Both overmatching and undermatching can have significant consequences to health care decision-making. Overmatches can result in automated clinical decision-making using records that do not actually belong to the patient. Undermatches can result in automated clinical decision-making being performed without full view of the patient's records. Either overmatching or undermatching can pose serious risks to the health of patients. For example, contraindicated medications and/or treatments may be administered to patients due to overmatching or undermatching patient records. Many health care organizations err on the side of undermatches because overmatches may result also in inappropriate disclosures. For example, an overmatch could result in private information in a patient record of one patient being exposed (without permission) to another patient. Consequently, currently known systems provide users with a dilemma of risking undermatching records (which causes clinical decision-making to miss relevant information, with potentially deadly consequences) or overmatching records (which causes clinical decision-making to be made on the basis of incorrect information, as well as inappropriately exposing private health information). An improved system is needed that avoids both undesirable outcomes of this dilemma. That is, a system is needed that correctly matches patient records to reduce clinical risks and avoid risking inappropriate exposure of private health information.

BRIEF DESCRIPTION

An artificial intelligence (AI) record matching system is provided. This system can include one or more processors at a healthcare management system that obtain patient records having demographic information. The processors may compare the demographic information in the patient records and determine that the demographic information in the patient records do not match. Responsive to determining that the demographic information in the patient records does not match, the processors may determine whether the demographic information in the patient records that do not match are linked with a common household by comparing the patient records using a first set of one or more rules, criteria, or parameters. Comparing the records using the first set of the one or more rules, criteria, or parameters may determine (a) whether the demographic information in the patient records that do not match include a common first name and a same date of birth and whether the patient records indicate membership in a common health care plan, (b) whether the demographic information in the patient records that do not match include personal identifiers that share at least a designated length of a character string, (c) whether the demographic information in the patient records that do not match include a common street address name, a common postal code, and the common first name and include a combination of a street address number and the common street address name is used by no more than a designated number of people, and/or (d) whether the demographic information in the patient records that do not match include the common street address name, the street address number, and the common postal code, and the combination of the street address number and the common street address name is used by no more than the designated number of people.

The processors may determine whether the non-matching demographic information includes exclusionary intra-family overmatching data according to the first set of one or more rules, criteria, or parameters responsive to determining that the demographic information in the patient records that do not match are linked to with the common household. The processors may determine whether the demographic information includes the exclusionary intra-family overmatching data by determining (e) whether the demographic information in the patient records that do not match include the common first name but different dates of birth that are within a designated time period of each other, (f) whether the demographic information in the patient records that do not match includes the same date of birth but different first names that include a designated nickname, a truncated variation of the first names, or initials of the first names, (g) whether the demographic information in the patient records that do not match include different character strings that have at least a designated length of identical characters, and/or (h) whether the demographic information in the patient records that do not match includes the different first names that differ by no more than a designated edit distance.

The processors may determine that the patient records include the medical information of a same person responsive to determining that the demographic information in the patient records that do not match are linked with the common household but do not include the exclusionary intra-family overmatching data or responsive to determining that the patient records do not all include the medical information of the same person responsive to determining that the demographic information in the patient records are not linked with the common household or include the exclusionary intra-family overmatching data. The processors may repeatedly receive feedback data indicative of one or more of overmatching or undermatching the patient records to each other using the first set of one or more rules, criteria, or parameters, the one or more processors configured be repeatedly trained based on the feedback data by repeatedly modifying the one or more rules, criteria, or parameters of the first set into a modified set of the one or more rules, criteria, or parameters that differs from the first set, the one or more processors configured to use the one or more rules, criteria, or parameters that are modified in the second set during repeated training of the one or more processors to reduce the one or more of overmatching or undermatching of the patient records during successive iterations of the one or more processors examining the patient records.

A method also is provided that includes examining patient records using an AI record matching system that compares the patient records using one or more rules, criteria, or parameters; determining whether any of the patient records include different demographic information but include same medical information for a same person based on comparing the patient records using the one or more rules, criteria, or parameters; receiving feedback data indicating an overmatching of the patient records to the same person or an undermatching of the patient records to the same person; training the AI record matching system by modifying the one or more rules, criteria, or parameters based on the feedback data; and iteratively repeating one or more of examining the patient records, determining whether any of the patient records include the different demographic information but the same medical information for the same person, receiving the feedback data, and training the AI record matching system.

An AI record matching system also is provided that includes one or more processors that may compare patient records using one or more rules, criteria, or parameters and determine whether any of the patient records include different demographic information but include same medical information for a same person based on comparing the patient records using the one or more rules, criteria, or parameters. The processors may receive feedback data indicating an overmatching of the patient records to the same person or an undermatching of the patient records to different patient identifiers. The processors may be trained by modifying the one or more rules, criteria, or parameters based on the feedback data. The processors may iteratively repeat one or more of examining the patient records, determining whether any of the patient records include the different demographic information but the same medical information for the same person, receiving the feedback data, and training the one or more processors.

BRIEF DESCRIPTION OF THE DRAWINGS

In the drawings, reference numbers may be reused to identify similar and/or identical elements.

DETAILED DESCRIPTION

Figure 1:
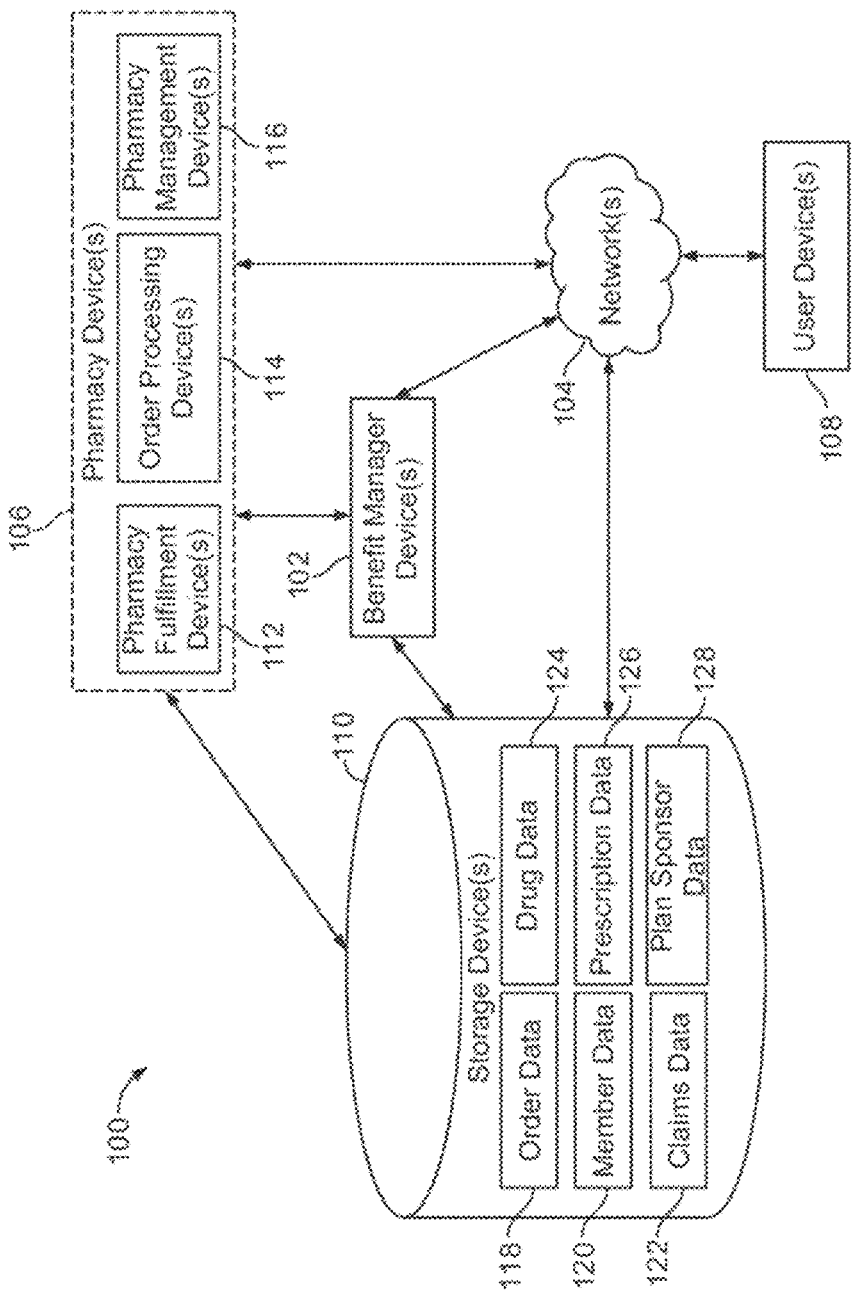
FIG. 1 is a functional block diagram of an example system including a high-volume pharmacy.

Example systems and methods for matching patient records are described herein. These record matching systems and methods examine demographic information in patient records to determine which patient records are associated with (e.g., include the health care information of) the same patient or the same patient identifier (e.g., a unique identifier of a person). The systems and methods can use the demographic information available to health care processors, such as patient identifiers, patient names, mailing addresses, dates of birth, family associations, health care coverage information, and the like. The systems and methods can examine the demographic information in the records to determine whether records represent patients in the same household. If the records do not contain demographic information indicating that the records represent patients in the same household, then the systems and methods determine that the records represent different patients.

If the system and method determine that the records represent patients in the same household, the system and method can then determine whether the records represent different persons in the same household. For example, the system and method can examine the demographic information to determine whether the records are associated with different people in the same households (e.g., twins living in the same household, a junior and senior relationship between parent and child, etc.). If the system and method determine that the records do not represent different patients within the same household, then the system and method determine that the records belong to the same patient or patient identifier.

The present disclosure described herein uses this two-step approach to allow for a less stringent confidence requirements in the second step. For example, the second step of intra-household examination of the household-related records to determine whether the records are associated with different people in the same household can be performed with a lower certainty or reduced requirement or threshold of confidence. Additionally, the separation of these steps can allow for customization of kinds of connections for certain types of patients. Patients with Medicare coverage, for example, tend to appear with certain demographic patterns while patients with employer health care coverage tend to appear with different demographic patterns. The connection algorithms used by the systems and methods described herein can be customized to these types of patterns.

The rules used by the systems and methods for individual record matching can ignore the record information used to make the family connection (e.g., the same household determination), yet account for pattern-matching within families. This allows the system or method to infer whether the data source for one or more of the records considers the distinct records to represent distinct persons. The system or method can use this consideration among the other information to determine (with increased confidence) that the records match (e.g., are associated with the same patient).

The systems and methods described herein improve the functioning of known computerized systems that attempt to match records with patients. As described herein, various rules are used to determine which records represent different patients to avoid overmatching records to patients (and thereby unlawfully exposing a patient's private health information to others) and avoid undermatching records to patients (and thereby risking serious health consequences such as death to a patient who is incorrectly associated with another person's medical record). For example, without the present disclosure described herein, computers that operate to automatically associate records with patients are at increased risk of overmatching and an increased risk of undermatching records to patients. But, with the unique rules and processes described herein, these risks are significantly reduced. Consequently, the functioning of the computers in matching records to patients is significantly improved as these computers will not or are less likely to overmatch or undermatch records to patients. Use of the subject matter described herein also provides a practical application of the subject matter with meaningful limitations as the processes provide specific improvements with the meaningful limitations to operation of the computers that match records to patients in a more accurate and reliable manner than the known processes used to match records to patients. Stated differently, the subject matter does not merely state that records are more accurately connected with patients. Instead, the subject matter described herein provides meaningful limitations on how specific rules and analyses are performed to improve the functioning of the computers that match records to patients.

As described below, all or part of the systems described herein may be an artificial intelligence (AI) or machine-learning system that can automatically perform the operations of the methods also described herein. These types of systems may be trained from outside information and/or self-trained to repeatedly improve the accuracy with how records are (or are not) matched to the same person. Over time, these systems can improve by matching records with increasing accuracy and speed, thereby significantly reducing the likelihood of dangerous consequences to health care decision-making that otherwise can result from overmatching and undermatching of the records to patients. The AI or machine-learning systems described herein may include technologies enabled by adaptive predictive power and that exhibit at least some degree of autonomous learning to automate and/or enhance pattern detection (e.g., recognizing irregularities or regularities in data of records), customization (e.g., generating or modifying rules to optimize record matching), or the like. The record matching system may be trained and re-trained using feedback from one or more prior analyses of the records. This feedback may indicate overmatching or undermatching of records to patients. Based on this feedback, the record matching system may be trained by adjusting one or more parameters, weights, rules, criteria, or the like, used in the analysis of the same or other patient records to better match the records to patients (e.g., by reducing overmatching and undermatching of records). This process can be performed using production data instead of training data, and may be repeated many times to repeatedly improve the matching of records to each other and to patients. The training of the record matching system minimizes false positives (e.g., overmatches of records) and/or false negatives (e.g., undermatches of records) by performing an iterative training algorithm, in which the record matching system is retrained with an updated set of production data and based on the feedback from the records examined prior to the most recent training of the record matching system. This provides a robust record matching model that can better determine whether records are associated with the same or different persons while limiting the number of false positives (e.g., incorrectly matching records to the same person or patient).

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long-term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the operations described above.

As part of the adjudication, a plan sponsor (or the PBM on behalf of the plan sponsor) reimburses the pharmacy for filling the prescription drug when the prescription drug was successfully adjudicated. The adjudication operations described above generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Va.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications. As used herein, the term common can be used to indicate that two or more things are the same. For example, a common name may be the same name, a common household may be the same household, and so on.

The prescription data 126 may include information regarding prescriptions that may be issued by prescribers on behalf of users, who may be members of the pharmacy benefit plan—for example, to be filled by a pharmacy. Examples of the prescription data 126 include usernames, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
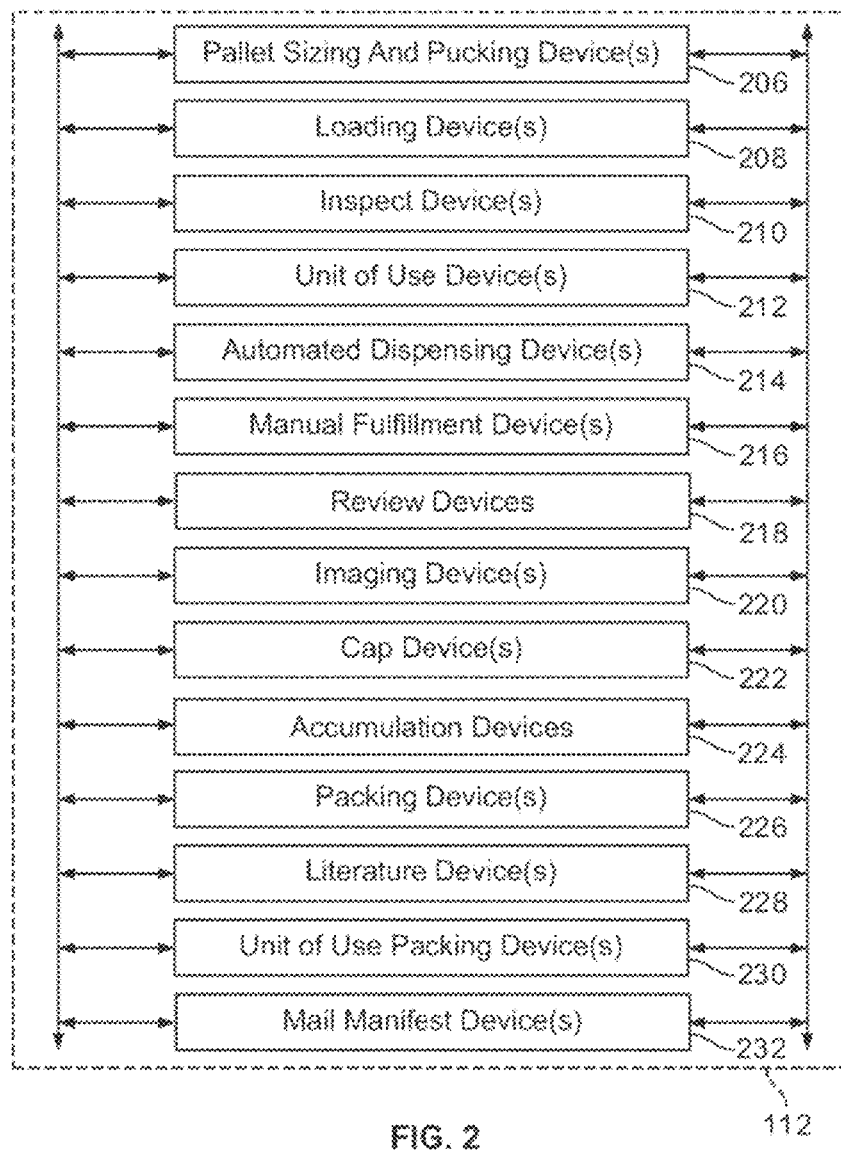
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be in the same area or in different locations. For example, the devices 206-232 may be in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among several discrete devices and/or combined with other devices.

Figure 3:
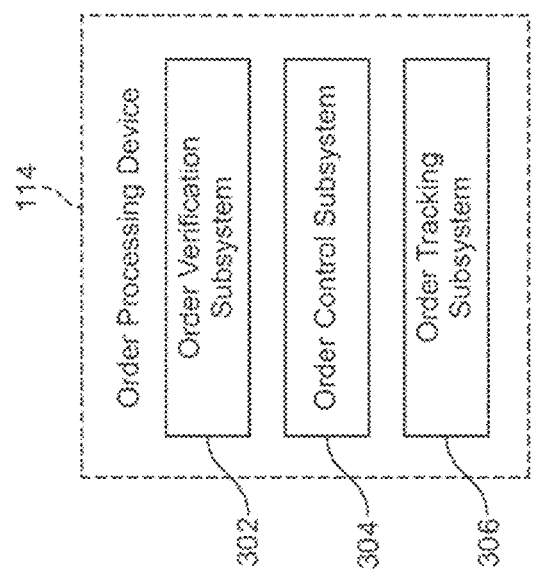
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Figure 4:
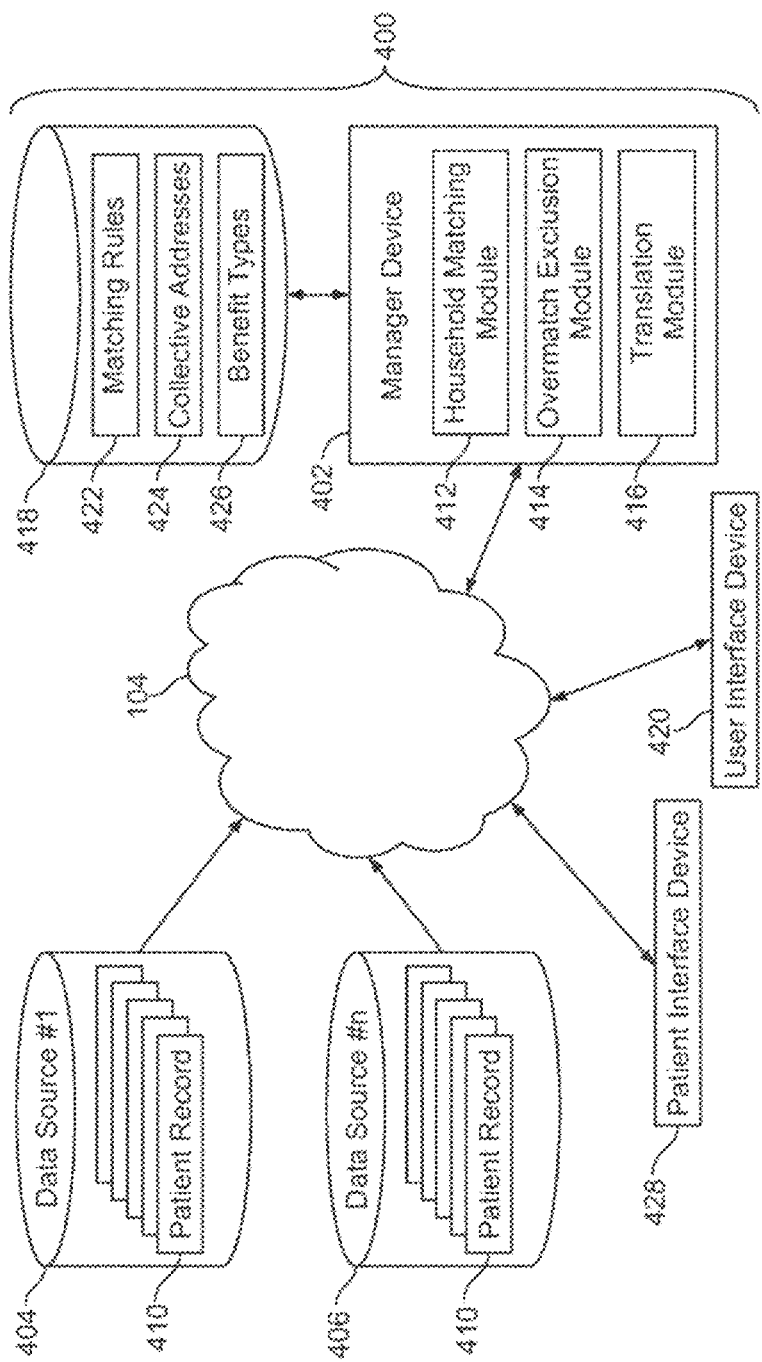
FIG. 4 is a block diagram of a patient record matching system, according to an example embodiment.

FIG. 4 is a block diagram of a patient record matching system 400, according to an example embodiment. The system 400 alternatively can be referred to as a healthcare management system. The system 400 can represent the benefit manager device 102 or at least part of the benefit manager device 102. The system 400 includes a record manager device 402 ("Manager Device" in FIG. 4) in communication with one or more data sources 404, 406 via one or more computer communication networks 104 (e.g., the Internet, an intranet, or other network). The record manager device 402 obtains multiple patient records 410 from one or more of the data sources 404, 406 and examines demographic information included in the patient records 410 to determine whether any two or more of the patient records 410 are associated with the same household and, if so, whether any two or more of the patient records 410 are associated with the same patient. The patient records 410 can be associated with the same patient when the patient records 410 include information on medication prescribed to the same person, health care services administered to the same person, health care payments made on behalf of the same person, or the like. The record manager device 402 may obtain and analyze many records as set forth herein to determine which records match to the same patient, even though the records may include different information that makes the records appear to be for different patients when mentally compared with each other by a person. The record manager device 402 may concurrently examine the information contained in many more records than could be reasonably mentally examined by a human being within a reasonable time period to determine whether the records include information of the same person. For example, then record manager device 402 may examine the information contained in tens of thousands, hundreds of thousands, or millions of medical records at the same time (e.g., concurrently or simultaneously) to determine which records include information associated with the same patient within a time period needed to make a medical decision (e.g., within a few seconds, such as three seconds; within a few minutes, such as three minutes; within a single day; or the like in different embodiments). Conversely, mentally comparing this many records may take many hours, days, weeks, months, or even years, which may be too long to provide information for medical decisions.

The record manager device 402 can be one or more computerized devices used by an operator to automatically determine whether patient records 410 belong to the same patient. Examples of the record manager device 402 include a set-top box (STB), a receiver card, a mobile telephone, a personal digital assistant (PDA), a display device, and a computing system, etc. Other devices, however, may also be used. In some embodiments, the record manager device 402 may include a mobile computing device. For example, the record manager device 402 may include a mobile electronic device, such an iPhone or iPad by Apple, Inc., mobile electronic devices powered by Android by Google, Inc., and a Blackberry by BlackBerry Limited. The record manager device 402 may also include other computing devices, such as desktop computing devices, notebook computing devices, netbook computing devices, gaming devices, and the like. Other types of electronic devices may also be used. For example, the record manager device 402 can represent other hardware circuitry that is connected to and/or includes one or more than one processor (e.g., one or more integrated circuits, one or more field programmable gate arrays, and/or one or more microprocessors) that perform the operations described herein in connection with the record manager device 402.

In one embodiment, the record manager device 402 is operated by an entity that is at least partially responsible for management of a pharmacy or drug benefit plan. While such an entity operating the record manager device 402 can be a pharmacy benefit manager (PBM), other entities may operate the record manager device 402 on behalf of the PBMs or other entities. For example, the record manager device 402 may be operated by a health plan or entity providing the health plan, a retail pharmacy chain, a drug wholesaler, a data analytics entity, or other type of software-related company, etc., or the like. In some embodiments, a pharmacy benefit manager that provides the pharmacy benefit may also provide one or more than one additional benefits including a medical or health benefit, a dental benefit, a vision benefit, a wellness benefit, a radiology benefit, an insurance benefit, a long-term care benefit, a nursing home benefit, etc., and the like. The pharmacy benefit manager may, in addition to operations of the pharmacy benefit manager, operate one or more than one pharmacies. The pharmacies may be retail pharmacies, mail order pharmacies, etc. While the description focuses on examining demographic information in patient records 410 to determine whether records 410 are associated with the same patient, not all embodiments of the present disclosure are limited to health care records. The demographic information of other types of records can be examined as described herein to determine whether the records belong to the same person.

The data sources 404, 406 represent two or more databases or other computer systems that store patient records 410. The data stores 404, 406 can include databases located at health care providers, health care payors, pharmacy benefit managers, etc. The record manager device 402 can communicate with the data sources 404, 406 via the network(s) 104 to obtain the patient records 410. For example, the record manager device 402 can receive identifying information about a patient that submits a request for a pharmacy benefit or another healthcare benefit to a pharmacy, health care facility, or other health care provider. This identifying information can include some information that identifies the patient, such as a name, address, or the like. The identifying information may not be unique to that patient. For example, one or more other patients may have the same (or substantially similar) identifying information. This can occur more often with persons having common (e.g., the same) names (e.g., Joe Smith), persons having addresses associated with many people (e.g., college dormitories, prisons, etc.), or the like.

Figure 5:
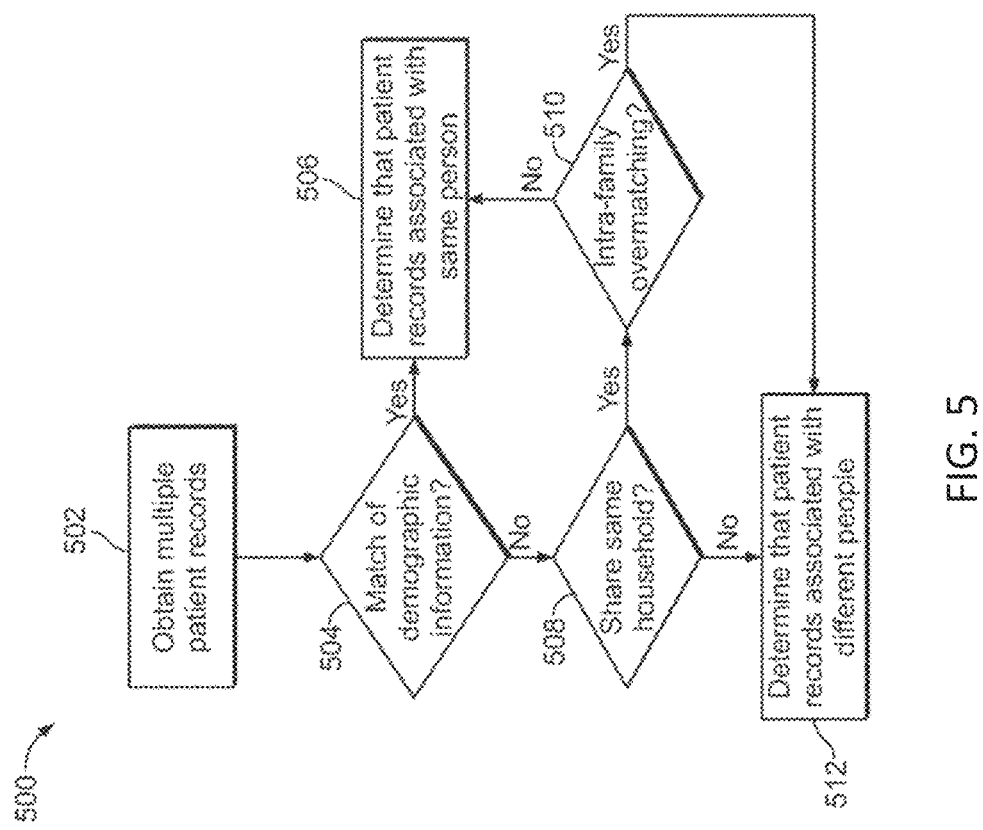
FIG. 5 illustrates a flowchart of one embodiment of a method for determining whether patient records match each other.

FIG. 5 illustrates a flowchart of one embodiment of a method 500 for determining whether patient records 410 match each other. The method 500 can represent operations performed by the record manager device 402 to determine whether multiple patient records 410 belong to or are otherwise associated with the same person.

Prior to performing the operations in the method 500, a preparatory activity of determining which different first names are nicknames of each other (or other versions of each other, such as one name being misspelled or truncated) to assist in later determining whether different records 410 belong to the same person or different persons. This activity can be performed on a repeated basis to identify commonly used nicknames (e.g., the same nickname), common misspellings (e.g., the same misspelling), and the like. The activity can be performed automatically and repeatedly to ensure that the association of nicknames, misspelled names, truncated names, etc., with corresponding names is repeatedly updated as naming and nickname trends change.

While some nicknames are identified by referring to using a database, list, table, or other memory structure that associates nicknames, frequently misspelled names (e.g., names that are misspelled more often than other names), truncated versions of names, etc. with each other, such a database, list, table, or other memory structure can heavily rely on manual upkeep and updating of the database, list, table, or other memory structure. This can introduce additional errors and result in many different names in records that belong to the same person being misidentified as belonging to different people. For example, nicknames can change over time, new names may become popular, and the like.

An additional feature of the subject matter describe herein can repeatedly determine which different first names are associated with each other as nicknames, truncated versions, misspellings, etc. This can reduce the likelihood of records belonging to the same person being mistakenly identified as belonging to different persons when at least one of the records includes a nickname, a misspelled name, a truncated name, or the like.

Figure 6:
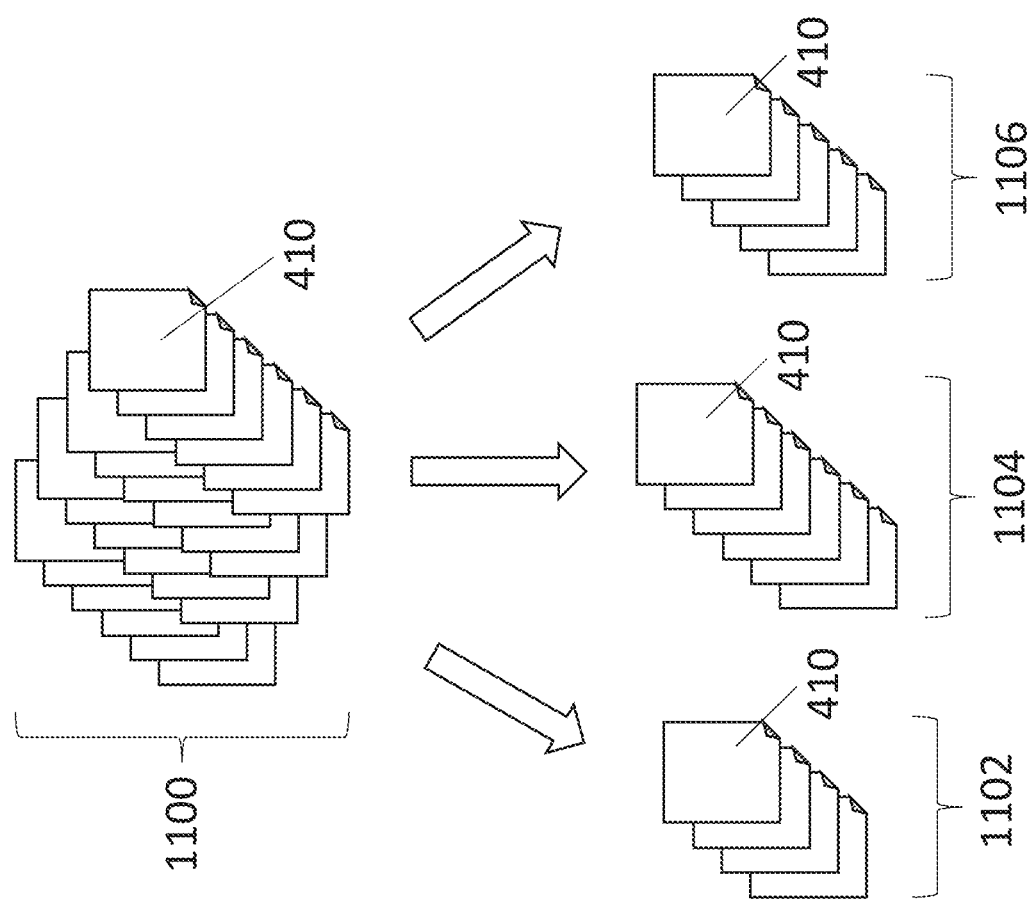
FIG. 6 illustrates a preparatory activity to determine combinations of first names that can be reliably treated as nicknames.

With continued reference to the system 400 shown in FIG. 4 and the flowchart shown in FIG. 5, FIG. 6 illustrates this preparatory activity to determine combinations of first names that can be reliably treated as nicknames. The manager device 402 can access or be provided with a large repository 1100 of demographic information. This repository 1100 can be a large set of the patient records 410 and/or can include other sources of information that are not medical or pharmacy records, such as databases or lists of names and other demographic information obtained or generated outside of a healthcare entity or environment. This other demographic information can include mailing addresses, social security numbers (or portions thereof), phone numbers, member identification numbers, etc.

The number of records 410 examined by the manager device 402 to identify nicknames or changes in trends in nicknames can be many more than those that are examined to determine whether the records 410 correspond to the same person (as described herein). For example, the manager device 402 can examine tens of thousands of records 410 from the repository 1100 to identify nicknames, while the manager device 402 can examine dozens records to determine whether these records 410 belong to the same person.

The manager device 402 can examine the records 410 from the repository 1100 and identify households having the same pair of different first names. For example, among the records 410 examined by the manager device 402 from the repository 1100 to identify nicknames (but not to match records 410 to the same person), the manager device 402 may discover that a first pair of first names (e.g., Patrick and Pat) are associated with the same household (e.g., same mailing address) in a first set 1102 of records 410, a second pair of first names (e.g., Christopher and Chris) are associated with the same household in a second set 1104 of records 410 (but a different household with which Patrick and Pat are associated), a third pair of first names (e.g., David and Joseph) are associated with the same household in a third set 1106 of records 410 (but a different household than with which Patrick and Pat are associated and with which Christopher and Chris are associated), and so on. The households that different pairs of first names appear in the records 410 will be different households. For example, the first set 1102 of records 410 in which the first pair of names appear in the same household may have thirty thousand different households listed in the records 410. This can occur because many different households may have both a Patrick and a Pat living in the household, or may have a single person that goes by the names Patrick or Pat. The manager device 402 examines the records 410 not just for different pairs of names in the same household among all records 410, but for pairs of names that are in the same household (even where the pairs of names may be in different households).

To consider whether a pair of different names are nicknames of each other, the manager device 402 can require that the number of instances where records 410 show the different names in the same household (even though different instances may be different households) share a unique demographic marker in at least a certain threshold proportion of households and/or volume of households in which the names co-exist. For example, if the proportion of instances where records 410 show the different names in the same household with the same demographic marker is no greater than this threshold, then the manager device 402 can determine that there is not enough confidence to determine that the different names are nicknames. But if the proportion and/or volume of instances where records 410 show the different names with the same demographic marker surpasses the threshold, then the manager device 402 can determine that there is enough confidence to determine that the different names are nicknames. Stated differently, a pair of different names can be identified as nicknames (or at least one name is a nickname of another name) when a likelihood of affinity between the different names exceeds a threshold. The likelihood of affinity can have a value that is based on the rate at which the different names share the same demographic information or markers having a distinguishing feature. For example, the likelihood of affinity can be greater when different names share the same social security number (or portion thereof) than when the different names share another value (e.g., person number or portion of a person number).

To determine whether the different names are nicknames, the manager device 402 can examine demographic markers in the records 410 within the set 1102, 1104, 1106. Using this information, the manager device 402 can determine likelihoods of affinity within a family unit. For example, the manager device 402 can examine how often the names in the records 410 in the set 1104 are associated with the same date of birth, the same social security number (or portion thereof), the same person number, etc., in the records 410. The more often that the pair of names appears in the records 410 in the set 1104 with other affinities, the more likely it is that the pair of names are different versions of the same name for the same person. For example, if Christopher and Chris frequently appear in the records 410 in the set 1104 with the same social security number or the same portion of a social security number, then Christopher and Chris are more likely to represent the same person (and therefore be nicknames of each other).

If two (or more) different first names appear in the set 1102, 1104, or 1106 of records 410 with the same demographic information more than a threshold number and/or threshold percentage of times (among all examined records or instances of the names), then the manager device 402 can determine that the two (or more) different first names are nicknames or different versions of the same name (e.g., with the different versions potentially being misspellings, truncations, etc. of at least one of the names).

The manager device 402 can apply one or more thresholds to determine which different first names in a set 1102, 1104, or 1106 are likely nicknames of each other. The manager device 402 can apply a low threshold that only requires that one piece or item of demographic information be the same between the two different names. For example, those names having at least one of the same mailing address, the same last name, the same social security number (or portion thereof), the same identification number (or portion thereof), etc., may be associated with the same family unit. Optionally, the manager device 402 can apply one or more greater thresholds to determine which different names belong to the same family unit. For example, the manager device 402 determine that two or more (or three or more, or four or more, and so on) of the same items of demographic information match each other when comparing records 410 in the same set 1102, 1104, or 1106 before determining that the names are nicknames of each other.

The manager device 402 can examine the groups (e.g., pairs) of names in a set 1102, 1104, 1106 of records 410 and measure how often each combination of these grouped names has the same distinguishing feature or a different distinguishing feature in the demographic information associated with each name in the group. If the percentage affinity of each is greater than a designated threshold, and occurs with sufficient volume for confidence, then the manager device 402 decides that the combination of names represent nicknames or different versions of the name for the same person. Otherwise, the names in the combination are not identified as nicknames or different versions of the same name. The name combination that is found to represent nicknames or the same versions of the name for the same person is then stored for use during patient record matching, as described herein.

Returning to the description of the method 500 shown in FIG. 6, at 502, multiple patient records 410 are obtained. The record manager device 402 can communicate with one or more of the data sources 404, 406 to obtain the patient records 410 that are associated with at least some of the identifying information received by the record manager device 402. For example, the record manager device 402 can obtain the patient records 410 having the same or similar name and/or mailing address as the identifying information. The record manager device 402 can obtain a set of patient records 410 to be examined for matching from a single data source 404, 406 or from multiple different data sources 404, 406. In one embodiment, less than all the records 410 stored at a data source 404 or 406 are obtained by the record manager device 402. Alternatively, all the records 410 stored at a data source 404 or 406 are obtained by the record manager device 402.

At 504, the record manager device 402 examines demographic information in the obtained patient records 410 to determine whether the demographic information in two or more of the patient records 410 identically match each other. In some instances, the demographic information in two or more records may identically match each other such that no further analysis of the demographic information is needed to determine that the records 410 correspond to the same person. For example, the patient name, address, date of birth, and identifier contained in one patient record 410 may identically match this same demographic information in another patient record 410. This identical matching of demographic information can indicate that these patient records 410 correspond to the same person. As a result, the record manager device 402 can determine that the two or more matching records 410 belong to the same patient. Flow of the method 500 can then proceed toward 506.

If the demographic information in two or more of the obtained records 410 do not identically match, however, then the records 410 may not be able to be matched without further analysis of the demographic information contained in the records 410. The demographic information can be further examined to determine (a) whether the records 410 are associated with persons in the same household and, if so, (b) whether the records 410 are associated with the same or different persons in the same household, as described below. As a result, flow of the method 500 can proceed toward 508.

The record manager device 402 can examine the demographic information in the records at 508, 510 (described below) to determine whether any of the records 410 are associated with or belong to the same person. The record manager device 402 includes modules 412, 414, 416 that examine demographic information in the obtained patient records 410 to determine whether any two or more of these patient records 410 match (e.g., belong to or are associated with the same patient). These modules 412, 414, 416 may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip, that perform the operations described herein in connection with the different modules 412, 414, 416.

The module 412 is a household matching module 412 that examines the demographic information in the obtained records 410 to determine whether the demographic information in two or more of the records 410 is associated with the same household. The module 414 is an overmatch exclusion module 414 that examines the demographic information in the records 410 found to share a household (by the household matching module 412) to determine whether the demographic information in these household-sharing records 410 indicates overmatching of the records 410 to the same person. For example, the overmatch exclusion module 414 can determine whether the records 410 include exclusionary intra-family overmatching data, such as data that represents names, dates of birth, identifiers, addresses, etc., of different persons, that match each other according to matching rules 422 used by the household matching module 412 to determine whether the records 410 are associated with the same household (as described herein). The translation module 416 can create or modify a database or other memory structure that organizes different portions of the demographic information in the records 410. The translation module 416 can organize or re-organize this information in a memory of the record manager device 402 and/or a database 418 used by the record manager device 402, as described below. The re-organized demographic information can be used to later determine whether two or more records 410 match the same person without repeating the household-matching and overmatching exclusion steps described herein.

Returning to the description of the flowchart of the method 500 shown in FIG. 5, at 508, a determination is made as to whether the obtained records 410 include demographic information associated with the same household. For example, the household matching module 412 can examine the demographic information to determine whether different records 410 share partial names and birth dates, share mailing addresses, share personal identifiers, or the like, that are associated with the same address. Additional details of how the demographic information can be examined to determine if a household is shared by multiple records 410 is provided below. If the household matching module 412 determines that the demographic information in the records 410 share the same household, then additional analysis of the demographic information may need to be performed to determine whether the records 410 are associated with the same person. As a result, flow of the method 500 can proceed toward 510. But, if the household matching module 412 determines that the demographic information in the records 410 do not share the same household, then the additional analysis of the demographic information may not be needed to determine that the records 410 are associated with the same person. As a result, flow of the method 500 can proceed toward 512.

The operation of 508 can be performed concurrently on a large set of records. For example, at 508, the method 500 may involve determining that a first patient record 410 is not associated with the same household as a second patient record 410 or the household of a third patient record 410 but may determine that the household of the first patient record 410 is associated with the household of a fourth patient record 410. If the method 500 also determines at 508 that the fourth patient record 410 is associated with the same household as the second patient record 410 and that the second patient record 410 is associated with the same household as the third patient record 410, then the method 500 can link these associations together and determine that all of the first, second, third, and fourth patient records 410 are associated with the same household. Alternatively, the operation of 208 can compare patient records 410 with each other to identify shared households. For example, the method 500 can compare demographic information of a first patient record 410 at 208 with the demographic information of a second patient record 410 to determine whether the first and second patient records 410 share a common household (e.g., the same household). This can be repeated for additional pairs of patient records 410 to identify shared households.

At 510, a determination is made as to whether the household-sharing records 410 are overmatched with each other. An overmatch can occur when the household-sharing records 410 include demographic information that is similar enough to each other to indicate that the records 410 are associated with the same person, but in fact are not associated with the same person. For example, an overmatch can occur when multiple records 410 share the names Bob and the same household, but one record 410 is associated with Robert Sr. and another record 410 is associated with Robert Jr. As another example, an overmatch can occur when multiple records 410 share the same birth date and the same household, but each of the household-sharing records 410 is associated with a different twin, triplet, etc. As another example, an overmatch can occur when multiple records 410 have the same surnames and similar truncated first names but are associated with spouses having similar names (e.g., Chris and Christine Smith).

As described in more detail below, an intra-family or intra-household overmatch can be identified by examining additional demographic information in the records 410. For example, the overmatch exclusion module 414 can determine whether multiple instances or pieces of demographic information in each of the household-sharing records 410 are similar or identical. If multiple instances of demographic information in each of the household-sharing records 410 are similar or identical, then the household-sharing records 410 are more likely to be associated with the same person. The overmatch exclusion module 414 optionally can determine whether household-sharing records 410 are associated with the same or different people in the same household based on a uniqueness intent of the provider of the records 410. Different data sources 404, 406 may include different types of demographic information in the records 410 stored at the data sources 404, 406. Depending on the different types of demographic information stored in the records 410 and how similar or dissimilar the different types of demographic information are in the records 410, the overmatch exclusion module 414 can determine that the household-sharing records 410 do or do not include an overmatch. As another example, the overmatch exclusion module 414 can determine whether household-sharing records 410 are associated with the same or different persons based on how similar the demographic information is in the records 410 and the healthcare benefit type associated with the records 410, as described below.

If the household-matching records 410 are found to include an overmatch at 510, then these records 410 having the overmatch are determined to not be associated with the same person. As a result, flow of the method 200 can proceed toward 506. If the household-matching records 410 are not found to include an overmatch, then these records 410 can be determined to be associated with the same person. As a result, flow of the method 500 can proceed toward 512.

At 506, the household-sharing records 410 are determined to be associated with the same person. The manager device 402 can communicate a signal to an end-user interface device 420 to notify the device 420 that the household-sharing records 410 are associated with the same person. Alternatively, the manager device 402 may provide details of the matching records 410 that are associated with the same person to the interface device 420 so the interface device 420 can use the information in the matching records 410 to make one or more decisions about the health care of the person. Alternatively, at 512, the household-sharing records 410 are determined to not be associated with the same person. The manager device 402 can communicate information in the records 410 that are associated with a patient, and not the information in the records 410 that is not associated with the patient, to the device 420.

The device 420 can represent one or more computerized devices used to interface with the patient record matching system 400. Examples of the device 420 include a mobile telephone, a personal digital assistant, a display device, a computing system, a mobile electronic device, a desktop computing device, a notebook computing device, a netbook computing device, and the like. The user interface device 420 can be used by healthcare providers, pharmacies, payors, pharmacy benefit managers, or the like, to determine or view the determination of whether two or more patient records 410 are or are not associated with the same person. The determination that the household-sharing records 410 are associated with the same person can be used in a variety of ways.

For example, a healthcare provider can decide whether to provide (or not provide) a healthcare treatment based on information contained in one or more of the matching records 410. One patient record 410 may not indicate any allergies, but a matching record 410 can indicate that the same person has a latex allergy. Based on the determination that these records 410 represent the same person, the healthcare provider may avoid administering a flu vaccine to this person due to the latex allergy. As another example, one patient record 410 may not indicate any previous issues with radiation contrast, but a matching record 410 can indicate that the same person had a prior adverse reaction when he or she received radiation contrast. Based on the determination that these records 410 represent the same person, the healthcare provider may avoid administering the same radiation contrast or may select a different imaging modality for the person.

A pharmacy may utilize the record matching system 400 to conduct an automated drug utilization review to ensure that a patient can safely consume a prescribed medication. This type of review can involve examining a complete history of the drugs and conditions in the medical history of the patient, which may be stored in several different patient records 410 that are maintained by several different sources 404, 406. If fewer than all the records 410 for the same patient are matched to the patient, then the medical history of the patient can be incomplete. If the medical history of the patient is incomplete, the automated drug utilization review may conclude that it is safe for a patient to consume the medication, when in fact it is not safe for the patient to consume the medication. With ineffective or inaccurate matching of patient records, the drug utilization review process may determine that the patient is previously unknown when there is relevant history available of the patient which should be considered for a complete drug utilization review. For example, a patient may change jobs and receive a new prescription card via her new employer. The patient may be prescribed ciprofloxacin by a health care provider that is not aware that the patient is already consuming tizanidine, a contraindicated medication to ciprofloxacin.

Without the record manager device 402 finding the records 410 that correspond with this patient before providing tizanidine to the patient, the patient may experience a severe drug-drug interaction between ciprofloxacin and tizanidine. This interaction may pose a significant risk to the health of the patient and can involve costly additional healthcare that would otherwise not be needed. But, with effective and accurate matching of patient records, the drug utilization review process may determine that this patient is the same person associated with another patient record 410 that was prescribed tizanidine. The pharmacy can identify the drug-drug interaction based on this more complete medical history obtained from the matching of patient records 410 and can contact the healthcare provider who may write, for example, a new prescription for amoxicillin (another antibiotic which does not have the drug-drug interaction with tizanidine).

As another example, a pharmacy benefit manager can use the record matching system 400 (e.g., via the interface device 420) to monitor patients for early prescription refills on behalf of health care payors. The pharmacy benefit manager can monitor patients to ensure that the patients are not over-consuming medications. With ineffective matching of patient records 410, this monitoring process may not see prior medical histories for some patients and erroneously allow the patients to obtain early refills of medications. This can significantly increase costs to the health care payor. For example, a patient may obtain a ninety-day prescription of metformin on December 28$^{th}$, which is recorded in a patient record 410. The patient may switch to a new Medicare Part D plan on January 1$^{st}$ and request an early refill of this same prescription on January 6$^{th}$. Without effective patient record matching, the pharmacy benefit manager may not obtain or determine that the record 410 having information on the December 28$^{th}$ prescription fill is associated with this same patient who received a prescription on January 6$^{th}$. The early refill on January 6$^{th}$ may be provided, thereby increasing costs to the payor. With effective patient record matching, the pharmacy benefit manager is notified by the record manager device 402 that the patient is requesting a refill well before the ninety-day refill period is over (by determining that the patient record 410 associated with the December 28$^{th}$ fill is associated with this patient). The pharmacy benefit manager can notify the pharmacy to hold off on filling the prescription until the ninety-day period of the December 28$^{th}$ fill is completed or more nearly completed. This helps avoid the additional costs to the payor that could occur without the patient record matching.

Figure 7A:
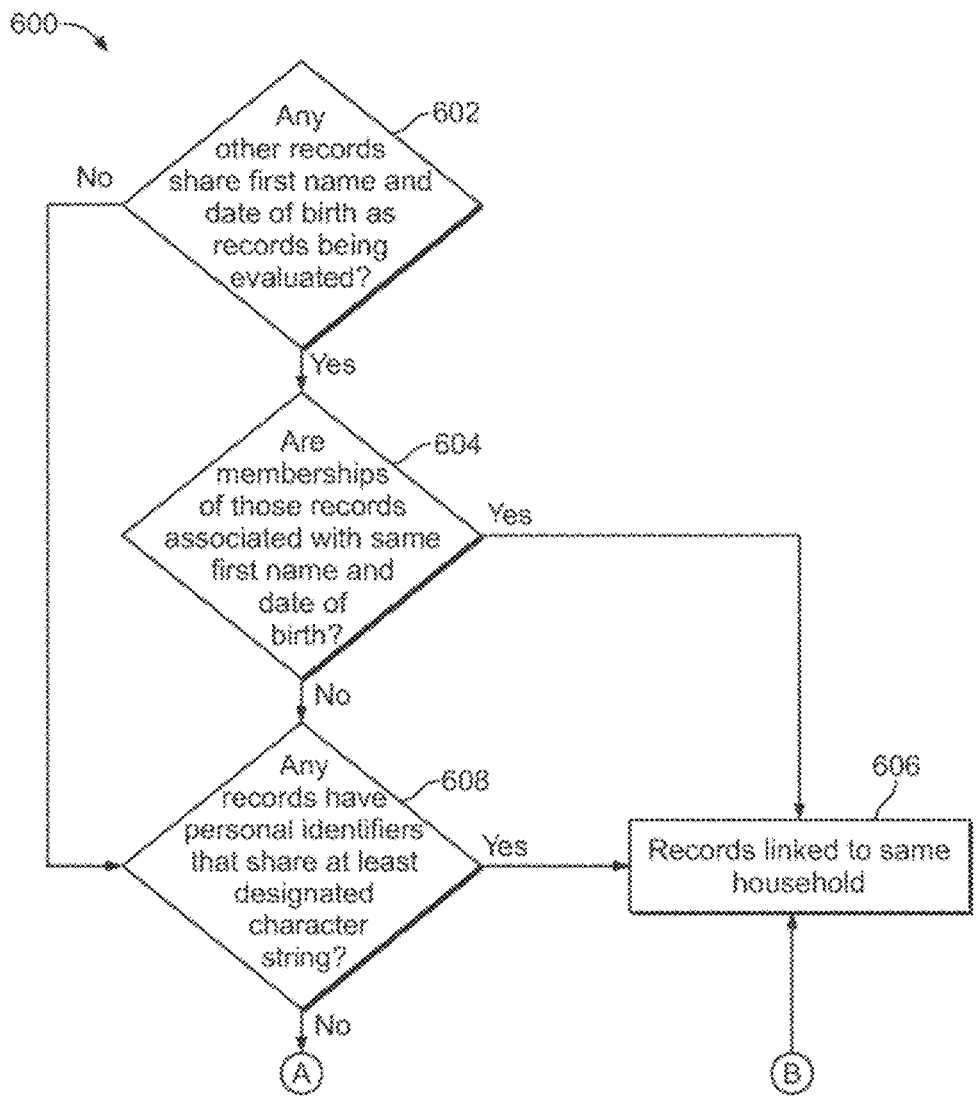
FIGS. 7A and 7B illustrate a flowchart of one embodiment of a method for determining which patient records are associated with a common household.
Figure 7B:
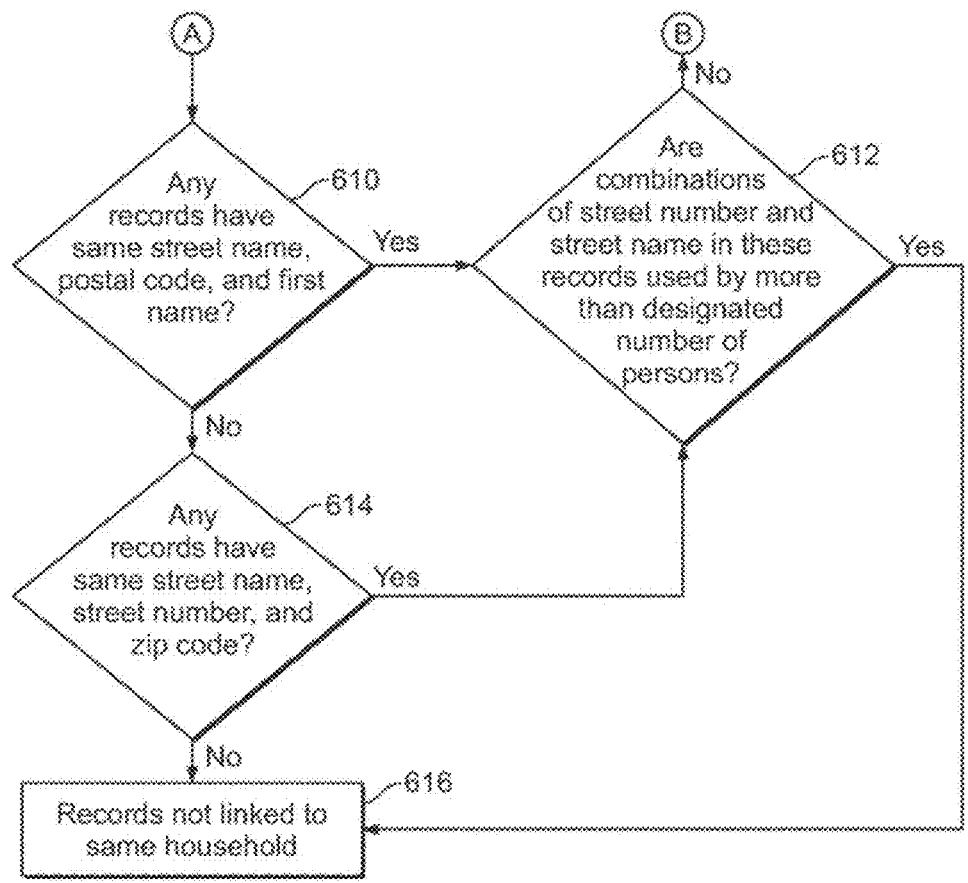

FIGS. 7A and 7B illustrate a flowchart of one embodiment of a method 600 for determining which patient records 410 are associated with a common household (e.g., the same household). The method 600 can represent additional operations performed in connection with 508 in the method 500 shown in FIG. 5. For example, the method 600 can include operations performed by the record manager device 402 to determine whether any patient records 410 are associated with a common household based on the demographic information contained in the records 410. As described above, the connection of records 410 to a common household can occur by linking the records 410 to each other via the common household. For example, the demographic information in a first patient record 410 may not indicate that the first patient record 410 and a second patient record 410 share the same household, but the demographic information in the first patient record 410 and in the third patient record 410 can indicate the same household and the demographic information in the second patient record 410 and in the third patient record 410 can indicate the same household 410. As a result, all the first, second, and third patient records 410 can be associated with the same household 410.

The household matching module 412 can use a variety of matching rules or algorithms 422 ("Matching Rules" in FIG. 4) to determine whether two or more records 410 are associated with the same household, whether these records 410 include demographic information that match each other or the records 410 are linked to each other by separating matching demographic information in at least a third record 410. The matching rules 422 are described in connection with the decisions made in the flowcharts shown and described herein. The matching rules 422 can be customized by the user or operator of the record manager device 402 as the need for more or less confident matching of records 410 is needed. The matching rules 422 can be stored in the database 418 shown in FIG. 4 or may be stored in another location.

At 602, a determination is made as to whether any demographic information in any patient records 410 being examined share a first name and a date of birth. The demographic information stored in a least some records 410 can include first names or forenames of persons, birth dates, and addresses. These names, birth dates, and addresses can be those names of the person(s) seeking healthcare, or can be the names, birth dates, and addresses of other people associated with the same membership to a health benefit plan.

The record manager device 402 can examine the demographic information of patient records 410 and determine whether two or more records 410 have the same first name and the same date of birth. If the records 410 have demographic information with the same first name and the same date of birth, then the household matching module 412 can determine that the records 410 potentially may share a household. As a result, flow of the method 300 can proceed toward 304. But, if the records 410 do not have demographic information with the same first name or the same date of birth, then the household matching module 412 cannot yet determine whether the records 410 share a household. As a result, flow of the method 600 can proceed toward 606.

At 604, a determination is made as to whether the demographic information in these same records 410 indicates that a membership to a health benefit plan with which one of the records 410 is associated also has a first name and a date of birth in a membership to a health benefit plan with which another record 410 is associated. A health benefit plan can be a health insurance plan, a pharmacy benefit plan, or other plan whereby patients receive medication or other health surfaces that are at least partially paid for by another party.

If a first patient record 410 and a second patient record 410 have the same first name and date of birth, and the membership to a health benefit plan with which the first patient record 410 is associated also has a first name and birth date that also occurs in the health benefit plan membership with which the second patient record 410 is associated, the record manager device 402 can conclude that the first and second patient records 410 share the same household. For example, a first patient record 410 is associated with a health benefit plan membership number 23456789 and include demographic information of a named member "Harry Potter" with a birth date of 31 Jul. 1980. A second patient record 410 can be associated with a different health benefit plan membership number 98765432 but may include demographic information of the same named member "Harry Potter" with the same birth date of 31 Jul. 1980. The addresses contained in the first and second patient records 410 are different, however. Therefore, the household matching module 412 cannot determine that the first and second records 410 are associated with the same household based on this portion of the demographic information alone.

The household matching module 412 can examine additional demographic information in the first and second records 410 that includes the name(s) and birth date(s) of one or more additional members of the health benefit plans. For example, the household matching module 412 can examine the first and second patient records 410 to determine that both memberships are associated with the same named member "Dudley Dursley" having the same birth date of 23 Jun. 1980. Based on this matching information, the household matching module 412 can determine that the first and second patient records 410 are associated with the same household. Flow of the method 600 can then proceed toward 606.

The additional name and birth date that is examined by the household matching module 412 may be a different name and/or birth date than the person that is seeking medication or other health care benefits. With respect to the preceding example, a person named "Harry Potter" may be attempting to refill a prescription or obtain an immunization at a health care provider. The health care provider can use the interface device 420 to submit the demographic information of "Harry Potter" to determine whether the prescription can be safely re-filled, or the immunization can be safely administered. In this example, however, the household matching module 412 uses demographic information of another person stored in the patient records 410 to determine that the patient records 410 are associated with the same household. The household matching module 412 does not necessarily use the demographic information of the person seeking the health care benefit to determine that the patient records 410 are associated with the same household.

At 606, the records 410 are determined to be associated with the same household. The household matching module 412 can determine that the first and second records 410 are associated with the same household and can report this determination to the overmatching exclusion module 414. Flow of the method 600 can terminate for these first and second records 410 but may be repeated for one or more additional records 410 to identify additional links between the records 410.

On the other hand, if the first patient record 410 and the second patient record 410 have the same first name and date of birth, but the membership to a health benefit plan with which the first patient record 410 is associated does not also have the first name or birth date that also occurs in the health benefit plan membership with which the second patient record 410 is associated, the record manager device 402 cannot yet conclude that the first and second patient records 410 share the same household at 604. As a result, flow of the method 600 can proceed toward 608.

At 608, a determination is made as to whether any of the patient records 410 have personal identifiers that share at least a designated length character string. A personal identifier can be a combination of letters, numbers, and/or symbols that is associated with an individual person, a family, or another group of persons by a health benefit plan provider or another entity. For example, personal identifiers in the patient records 410 can be client-assigned membership numbers, social security numbers, Medicare beneficiary numbers, or the like. Because different records 410 may be generated or maintained by different entities, the different records 410 for the same person may not include the same personal identifier.

The household matching module 412 can examine the personal identifiers stored in different records 410 to determine whether any personal identifiers share at least a designated length character string. The longer that the designated length is, the greater confidence or probability there is that the records 410 are associated with the same household. In one embodiment, the household matching module 412 can determine whether any personal identifiers in different records 410 share at least a character string that is at least a designated length (e.g., number of characters) long. In one example, this designated character string length is eight, but may be a longer or shorter length or number of characters. Optionally, the personal identifiers can be examined by the household matching module 412 to determine whether the personal identifiers have at least a designated number of matching characters, regardless of whether the characters are in a continuous string. For example, the records 410 may match when the records 410 include social security numbers that have at least eight of the same numbers within each of the social security numbers. But, if fewer than eight of the numbers match, the household matching module 412 may still determine that the records 410 share a household if the other two numbers in at least one of the social security numbers are an adjacent transposition of the numbers in a social security number in the other record 410. For example, if a first record 410 has the social security number 123-45-6789 and a second record 410 has the social security number 123-54-6789, then the first and second records 410 can be identified as matching each other or sharing a household. Alternatively, the household matching module 412 can determine whether any personal identifiers in different records 410 share at least a longer or shorter character length string. Some health care payors and providers create personal identifiers by adapting another identifier (e.g., a social security number) and adding or removing characters. Matching an eight-character string enables an automated match in those scenarios, with a one hundred million-to-one likelihood that the household match is not random.

If the personal identifiers in different records 410 share at least the designated length character string, then the household matching module 412 determines that these records 410 are associated with the same household. As a result, flow of the method 600 can proceed toward 606, which is described above. If the personal identifiers in different records 410 do not share at least the designated length character string, then the household matching module 412 cannot yet determine that these records 410 are associated with the same household. As a result, flow of the method 600 can proceed toward 610.

For example, a first record 410 may include a membership number of 0689273868 and a second record 410 may include a social security number 68927386. The household matching module 412 can determine that these records 410 are associated with the same household because these records 410 share at least the eight-character string of 6892738. As another example, a third record 410 may include a Medicare beneficiary identification number of K798098299. The household matching module 412 may not yet determine that the third record 410 shares a household with either the first or second record 410 due to the third record 410 not including an identifier that shares at least the designated length character string with the personal identifiers of the first or second records 410.

As described above, the household matching module 412 can examine the demographic information of other persons associated with the patient records 410 to determine whether the records 410 share a household. For example, the first patient record 410 can include a membership number of 0678239868 and the second patient record 410 can have a membership number 7092830929, which do not share at least the designated length character string. But the first patient record 410 having the membership number 0678239868 also can include demographic information of another plan member having social security number 037782905. The second patient record 410 having the membership number 7092830929 also can include demographic information of another plan member having social security number 037782905. Because the social security number of this additional member associated with each of the first and second patient records 410 matches, the household matching module 412 can determine that the first and second patient records 410 are associated with the same household.

At 610, addresses of the demographic information in the records 410 are compared. The household matching module 412 can examine demographic information in addition to the addresses in the records 410 to determine whether there are sufficient similarities to determine that the records 410 are associated with the same household. For example, the household matching module 412 can examine address information and first names in the records 410 to determine whether a street name, the zip code (e.g., postal code), and first name in one record 410 matches a street name, zip code, and first name in at least one other record 410. If the records 410 have the same street name, zip code, and first name, then the household matching module 412 can determine that the records 410 are more likely to share a household. In one embodiment, however, the household matching module 412 cannot yet determine that the records 410 are associated with the same household, only that the records 410 are more likely to share a household. The household matching module 412 may need to conduct additional examination of the addresses before determining whether the records 410 are or are not associated with the same household, as described below. Responsive to determining that the records 410 have the same street name, zip code, and first name, flow of the method 600 can proceed toward 612. If, however, the records 410 do not have the same street name, zip code, or first name, then flow of the method 600 can proceed toward 614.

Alternatively, it may not be necessary to match a street, zip code, and name between records 410. Instead, the demographic information can be examined to determine whether the street name, zip code, and a first name match between the records 410 and the address is not associated with a collective address (described below). If the records 410 share the same street name, zip code, first name, and the address is not a collective address, then the household matching module 412 can determine that the records 410 are associated with the same household. As another option, the demographic information can be examined to determine whether the street name, street number, and zip code match between the records 410 and the address is not associated with a collective address (described below). If the records 410 share the same street name, street number, and zip code, and the address is not a collective address, then the household matching module 412 can determine that the records 410 are associated with the same household.

In one embodiment, the records 410 have the same street name when the specific name of the street matches, regardless of whether the generic name of the street matches. The generic name of the street can be less specific than the specific name, such as "Boulevard," "Street," "Avenue," or the like. The specific name of the street is less common, such as "Leland," "Carobeth," "Main," or the like. Optionally, the records 410 have the same street name when the specific name of the street matches and regardless of whether the generic name of the street matches, whether a cardinal direction in the address matches. For example, the addresses "North Main Street" and "Main St." may be identified as matching, even though the cardinal directions do not match (or are missing) and/or the generic street name is abbreviated in one address. In one embodiment, the records 410 have the same street name when the specific name of the street matches, when the generic name of the street matches, and when a cardinal direction in the address matches. Alternatively, fewer than all these matches may be required.

At 612, a determination is made as to whether the street numbers and street names in the records 410 are associated with more than a designated number of residents. For example, the household matching module 412 can determine whether the matching address that is in the records 410 is associated with many residents. Certain addresses of a street number and a street name (e.g., 2268 E Morton, 918 W Illinois) may be associated with buildings known to have many temporary or long-term residents. Examples of these types of buildings include prisons, college dormitories, high rises, etc. Due to the large number of people that reside in these types of buildings, the matching of a street number and street name associated with such a building in the records 410 is less likely to indicate that the records 410 are associated with the same household (e.g., the same person in that household) than if the matching street number and matching street name was associated with a building having fewer residents.

Identifications of street numbers and street names associated with buildings having more than the designated number of residents can be stored in the database 418 as collective addresses 424. The list of collective addresses 424 can be modified by adding, removing, and/or changing addresses as the record matching system 400 and/or operator of the system 400 learn of additional buildings having large number residences. The household matching module 412 can refer to the collective addresses 424 in making the determination at 612 as to whether the street numbers and street names in the records 410 are associated with more than a designated number of residents. In one embodiment, the designated number of residents for an address to be identified as a collective address is 250 residents. Alternatively, a smaller or larger threshold of residents may be used to define a collective address.

If the matching address in the records 410 (determined at 610) is not associated with a collective address 424 having more than the designated number of residents, then the records 410 can be identified as being associated with the same household. Flow of the method 600 can proceed toward 606, which is described above. But, if the matching address in the records 410 (determined at 610) is associated with a collective address 424 having more than the designated number of residents, then the records 410 cannot be identified as being associated with the same household. Flow of the method 600 can proceed toward 616. Alternatively, the records 410 having demographic information associated with a collective address 424 can still be determined to share a household. If the household matching module 412 determines that a greater amount of information in the records 410 associated with the collective address matches, then the records 410 can be identified as sharing a household. For example, for a collective address, if the records 410 have demographic information that has matching street names, street numbers, zip codes, dates of birth, and first names, then the records 410 can be identified as sharing the same household (and flow of the method 600 can proceed from 612 to 606).

At 614, the demographic information in the records 410 are examined to determine whether the records 410 have the exact same street name, street number (e.g., building or house number), and zip code. The determination performed at 610 does not require the records 410 to have the exact same street number to proceed to 612 so long as first names in the records 410 match, as described above. In contrast, the determination performed at 614 does not examine first names in the records 410, but examines the street names, street numbers, and zip codes. If the street name, street number, and zip code in one record 410 matches the street name, street number, and zip code in another record 410, then flow of the method 600 can proceed toward 612, which is described above. For example, the address associated with the matching street number, the matching street name, and the matching zip code can be compared to the list of collective addresses 424 to determine whether the address is a collective address, as described above. If the street name, street number, and zip code in one record 410 does not match the street name, street number, and zip code in another record 410, then flow of the method 600 can proceed toward 616.

At 616, the records 410 are not identified as sharing the same household. The household matching module 412 can determine that the demographic information in the records 410 does not indicate that the records 410 are associated with the same household. As a result, the household matching module 412 can determine that the records 410 are associated with different persons (e.g., at 512 in the method 500 shown in FIG. 5).

Figure 8:
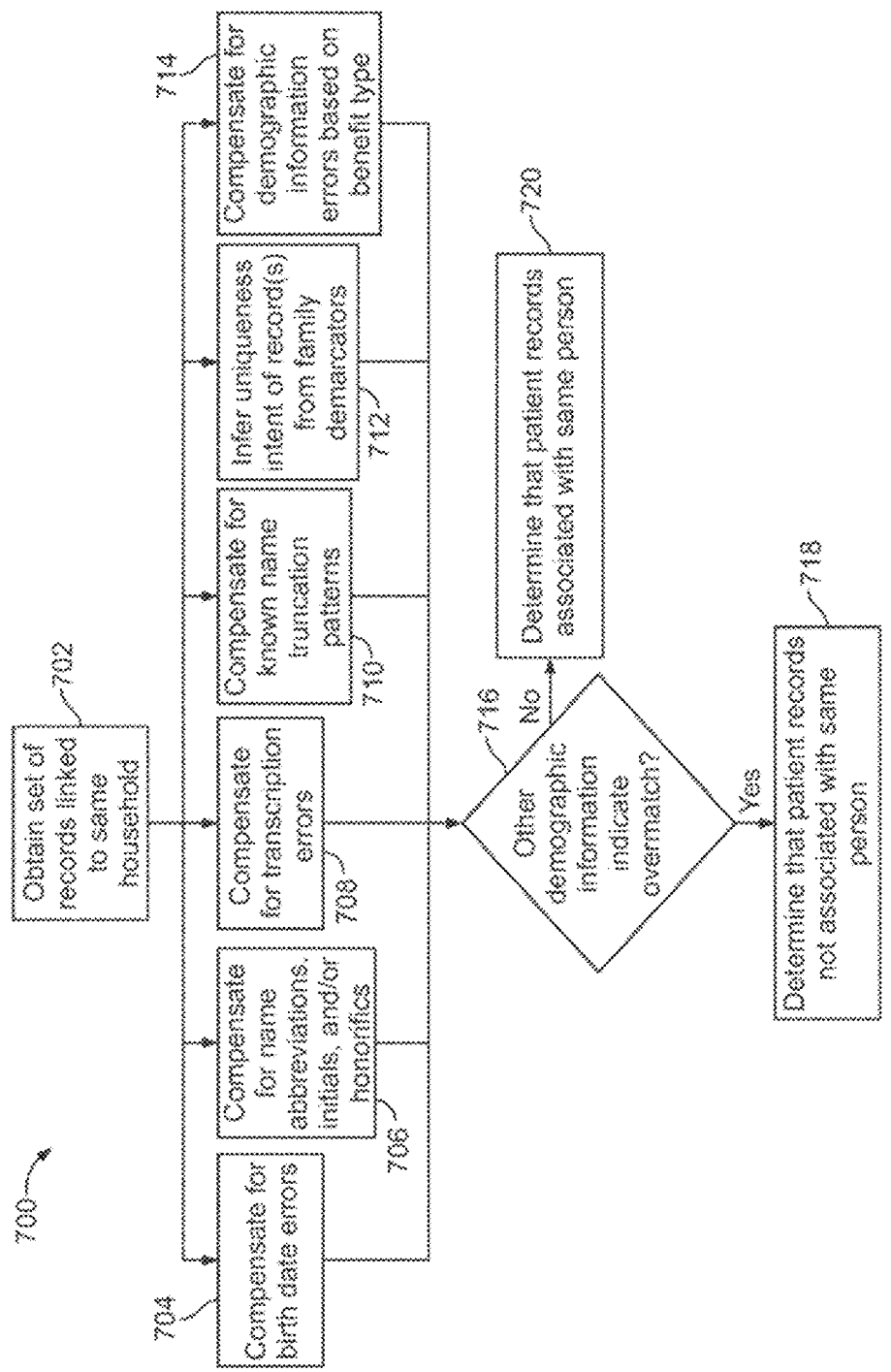
FIG. 8 illustrates a flowchart of one embodiment of a method for determining whether the demographic information in household-sharing patient records indicates an overmatch of the records.

FIG. 8 illustrate a flowchart of one embodiment of a method 700 for determining whether the demographic information in the household-sharing patient records 410 indicates an overmatch of the records 410. As described above, an overmatch of records 410 can occur when records 410 associated with different people are erroneously identified as being associated with the same person. The method 700 can be performed by the overmatch exclusion module 414 to ensure that the household-sharing records 410 associated with different persons are not incorrectly identified as being associated with the same person.

At 702, the set of records 410 identified as sharing a household is obtained. In one embodiment, the household matching module 412 can send and/or identify the records 410 identified as belonging to the same household at 508 in the method 500 shown in FIG. 5 and/or identified at 606 in the method 600 shown in FIGS. 7A and 7B to the overmatch exclusion module 414.

The overmatch exclusion module 414 can examine the demographic information contained within the household-sharing records 410 by compensating for minor variations in the demographic information (e.g., at 704, 706, 708, 710, 714) and/or by inferring a uniqueness intent of the records 410 (e.g., at 712) according to the rules 422. These compensations and inferences are described below and are used to prevent undermatching of records 410. For example, the compensations and inferences described below in connection with 704, 706, 708, 710, 712, 714 can be used to ensure that minor typographical errors, known nicknames, transcription errors, and the like, do not prevent records 410 that are associated with the same person from being identified as associated with the same person at 716 in the method 700.

While these compensations and inferences are described in a sequential order below, the compensations and inferences may be applied concurrently and/or in another order. If the demographic information using the compensations and/or inferences described in connection with 704, 706, 708, 710, 712, 714 indicate that an overmatch exists at 716 (e.g., that the records 410 do not represent the same person), then flow of the method 700 can proceed from 716 toward 718. At 718, the records 410 are determined to not represent the same person. But, if the demographic information using the compensations and/or inferences described in connection with 704, 706, 708, 710, 712, 714 does not indicate that an overmatch exists (e.g., that the records 410 do represent the same person), then flow of the method 700 can proceed from 716 toward 720. At 720, the records 410 are determined to represent the same person.

As one example, if the first name and date of birth in each of the household-sharing records 410 match the other household-sharing record 410 or household-sharing records 410, then these records 410 are determined at 416 to represent the same person at 416. Because the first name and date of birth in the records 410 exactly match across or between the household-sharing records 410, there is no need to compensate or infer anything in connection with these records 410 before determining that the records 410 are associated with the same person.

At 704, errors or minor differences in dates of birth between the household-sharing records 410 are examined to determine (at 716) whether an overmatch exists between these records 410. The overmatch exclusion module 514 can determine whether the household-sharing records 410 include the same first name but have dates of birth within a designated time period. This time period optionally can be referred to as a designated chronologic range. This designated time period can be one year or another period of time. For example, if a first record 410 includes the name Howard and the birth date 15 Nov. 1975, a second record 410 includes the same name Howard and the birth date 25 Jan. 1976, and the designated time period is one year, then the overmatch exclusion module 514 can determine that these records 410 represent the same person at 716.

As another example, the overmatch exclusion module 514 can determine whether the date of birth in the household-sharing records 410 is the exact same and whether names in these same records 410 are known nicknames of each other. Known nicknames can be designated names that are grouped together as being different versions of the same name. The known nicknames can be stored in the database 418, such as in part of the matching rules 422. As one example, a set of known nicknames can include Richard, Rich, Rick, and Dick. As another example, another set of known nicknames can include Chris, Christopher, Topher, and Kit. As another example, another set of known nicknames can include Peggy, Margaret, Peg, and Madge. If a first record 410 includes the name Richard and the birth date 15 Nov. 1976, and a second record 410 includes the name Dick and the birth date 15 Nov. 1976, then the overmatch exclusion module 514 can determine that these records 410 represent the same person at 716.

Additional compensations that can be performed include compensating for known name truncations at 710. Different records 410 that represent the same person can have different truncated versions of the same name due to data entry limitations, data entry errors, or the like. The overmatch exclusion module 414 can refer to a list of known truncated versions of names to determine whether different versions of the same name are used in different records 410. For example, the overmatch exclusion module 414 may determine that Christopher in one record 410 is the same as Christop in another record 410, is the same as Chris in another record 410, and is the same as Christoph in another record 410.

Additional compensations that can be performed include compensating for name initials at 706. Some records 410 that represent the same person can use initials instead of full names. The overmatch exclusion module 414 can refer to a list of known initials of names to determine whether different versions of the same name are used in different records 410. For example, the overmatch exclusion module 414 may determine that H Sragow in one record 410 represents the same person as Howard Sragow in another record 410 due to both these records corresponding to the same household, having the same last name, and having an initial in one record 410 that corresponds with the first letter in the first name of another record 410.

Additional compensations that can be performed include compensating for different versions of the same honorifics at 706. Some records 410 can include honorifics such as Dr., Jr., Sr., III, etc. The overmatch exclusion module 414 can ignore the inclusion of an honorific in a first record 410 if other information in a second record 410 otherwise matches the first record 410 (but for the inclusion of the honorific).

Another compensation that can be performed includes compensating for errors such as transcription errors, data entry errors, typographical errors, and the like, at 708. The demographic information in one record 410 may be nearly the same as the demographic information in another record 410. But it may be difficult to determine whether the differences between the demographic information in the records 410 is due to the records 410 being associated with different persons or due to the records 410 having typographical errors in the demographic information. The matching rules 422 can define restrictions on what differences or combinations of differences between the demographic information in household-sharing records 410 indicate that these records 410 are associated with different persons and what differences or combinations of differences between the demographic information in household-sharing records 410 do not indicate that these records 410 are associated with different persons (i.e., and may still represent the same person).

For example, values of demographic information in household-sharing records 410 that have at least a designated length character string in common may indicate that the records 410 represent the same person even though the values are not identical, so long as a designated portion of the values are identical. The overmatch exclusion module 414 can require that the last digit of a value in the demographic information be the same and that a designated length of a character string in the demographic information be the same across household-sharing records 410 to determine that these records 410 represent the same person. As one example, social security numbers are assigned by states, which can result in different persons in the same state having similar social security numbers. If other demographic information in the household-sharing records 410 is close to matching, then additional scrutiny can be used to determine whether the records 410 are an overmatch. For example, household-sharing records 410 having the same date of birth, nearly the same social security numbers, and first names that are known nicknames, then the overmatch exclusion module 414 can require additional examination of the social security numbers to determine if an overmatch exists. If John is born in Buffalo, N.Y. and Jack was born in Brooklyn, N.Y. on the same day, it is likely that the social security numbers assigned to John and Jack will be very similar or nearly identical. Because the names John and Jack are known nicknames, the records 410 associated with John and Jack have similar social security numbers, and John and Jack have the same birthdate, the overmatch exclusion module 414 can require that the last digit of the social security number in household-sharing records 410 be the same before determining that these records 410 represent the same person.

The matching rules 422 can identify certain portions of demographic data as being critical values. In continuing with the preceding example, the last digit or two of a social security number may be identified as a critical value. As another example, the first letter of a name may be a critical value. The overmatch exclusion module 414 may require that all critical values in demographic information in household-sharing records 410 be identical before determining that these records 410 represent the same person, regardless of other matches between other values of demographic information in the records 410.

Some records 410 can include demographic information that only slightly differs from demographic information in another record 410. For example, if a name in one household-sharing record 410 only differs from a name in another household-sharing record 410 by less than a designated amount (e.g., a designated edit distance), then the overmatch exclusion module 414 can determine that these names are the same. The edit distance can represent a minimum number of operations needed to transform a character string of one name in one record 410 to exactly match the character string of a name in another record 410. One type of edit distance can be a Levenshtein edit distance, which is the sum of the total number of replaced characters, the total number of character removals, and the total number of character editions. For example, the name Angelo in one record 410 and Angela in another record 410 can have an edit distance of one because the minimum number of operations needed to transform Angelo to Angela is one (replace the o with an a).

The overmatch exclusion module 514 also can infer a uniqueness intent of the demographic information in the household-sharing records 410 from the family demarcators used in the records 410 at 712. A family demarcator can be information provided to a health care provider, payor, or benefit manager by one or more members of a household that is common (e.g., the same) to two or more different members of the same household. For example, some records 410 may have the same social security number listed for all members of a family. The overmatch exclusion module 514 can examine additional information in the records 410 when a common family demarcator is used for multiple members in the records 410 to determine the uniqueness intent of the family demarcator. The uniqueness intent of the family demarcator can be determined based on the similarity or dissimilarity of other information in the records 410. As one example, the same social security number may appear in multiple records 410 associated with different names of members of the same household. For example, a first record 410 may have the name Johnny Smith, a second record 410 may have the name Alicia Smith, and a third record 410 may have the name Chad Smith, with each of the first, second, and third records 410 also including the exact same social security number. By itself, this social security number cannot be used to determine that any two or more of these records 410 are associated with the same person, even though these records 410 are all determined to be associated with the same household. In another example, if a fourth record 410 includes the name "Johnny," a fifth record 410 includes the name "Johannes," and both the fourth and fifth records 410 include the same social security number, then the overmatch exclusion module 414 can determine that the similarities in the names combined with the common usage of the social security number and the same household associated with these records 410 indicates that the fourth and fifth records 410 are the same person.

As another example, if multiple household-sharing records 410 have the same membership number, date of birth, gender, and first letter of the first name, have first names with an edit distance of one, share at least a designated character string length (e.g., eight characters) in social security numbers, have the same last digit of social security numbers, and each use a single social security number that does not appear on any other dates of birth within the membership associated with these records 410, then the overmatch exclusion module 414 can determine that the records 410 represent the same person. Optionally, the matching of social security numbers does not need to be a single continuous string for the household-sharing records 410 to be identified as representing the same person. For example, social security numbers in household-sharing records 410 may be identified as being associated with the same person (thereby indicating an overmatch) if the social security numbers differ by only a single digit (as long as the differing digit is not the last digit) or the social security numbers differ only by a transposition of adjacent digits. If a first household-sharing record 410 has the social security number 710-93-2276 and a second household-sharing record 410 has the social security number 710-83-2276, then these records 410 can be identified as representing the same person because all digits but the fourth digit match each other, and the last digits are the same. As another example, if a third household-sharing record 410 has the social security number 710-93-2276 and a fourth household-sharing record 410 has the social security number 710-93-2275, then these records 410 can be identified as representing different people because the last digit differs. In another example, if a fifth household-sharing record 410 has the social security number 710-93-2217 and a sixth household-sharing record 410 has the social security number 710-92-3217, then these records 410 can be identified as representing the same person because the only difference between the social security numbers is a transposition of adjacent digits (e.g., 32 instead of 23).

If multiple household-sharing records 410 have the same membership number, have the same date of birth, have similar first names (e.g., the edit distance of the names is one), have first names that are repeatedly associated within a health benefit plan membership with the same personal identifier, and use the same social security number that is not associated with any other dates of birth with in the health benefit plan membership, then the overmatch exclusion module 414 can determine that these records 410 represent the same person.

The overmatch exclusion module 414 can compensate for errors in the demographic information contained in one or more household-sharing records 410 to determine that the records 410 are associated with the same person based on a type of a health benefit plan associated with the records 410. Different types of health benefit plans have different associations with membership identifiers and members of the plan. For example, Medicare assigned member numbers to a group of members, but assigns a unique benefit identifier to individual members. As another example, some private health insurance plans assign group numbers to all covered members of a family. Workers Compensation memberships may have a unique identifier for each member, so the overmatch exclusion module 414 can allow for greater differences between household-sharing records 410 when the same Workers Compensation identifier is used (to determine that these records 410 represent the same person). Additionally, the overmatch exclusion module 414 can learn or be programmed to accept different types of errors based on a designated type of health benefit plan, while still determining that household-sharing records 410 represent the same person even if certain demographic data does not match. For example, certain types of benefit plans are more likely to have typographical or data entry errors in birth dates of records 410. If the household-sharing records 410 are associated with one of these benefit plans (e.g., the records 410 come from one of these benefit plans), then the overmatch exclusion module 414 may determine that the records 410 represent the same person even if there are differences between birth dates in the records 410. The different types of errors common to different benefit types, the number of members associated with membership numbers by the different benefit types, and the like, can be stored in the database 418 as benefit type data 426 ("Benefit Types").

The record manager device 402 may be required to examine the demographic information contained in a large number of records 410 within a short period of time to determine which records 410 are associated with the same household and whether two or more of the records 410 associated with the same household represent the same person. The record manager device 402 can perform the comparisons of demographic information contained in the records 410 using batch SQL in one embodiment so that a large number of decisions about the records 410 can be made at the same time. Alternatively, the record manager device 402 can perform these comparisons using procedural code.

In one embodiment, the translation module 416 shown in FIG. 4 can create or modify a database that organizes different portions of the demographic information in the records 410 to enable connections between records 410 to be available simultaneously. This can allow for any possible connection between records 410 to be properly made. The translation module 416 can create or modify a database so that each of the connecting data elements in the demographic information of the records 410 are organized into a name and value. The translation module 416 can organize or re-organize this information in a memory of the record manager device 402 and/or a database 418 used by the record manager device 402. The re-organized demographic information can be used to later determine whether two or more records 410 match the same person without repeating the household-matching and overmatching exclusion steps described herein. The translation module 416 can create this re-organized demographic information without changing the demographic information contained in any of the records 410. For example, because the records 410 may be provided by data sources 404, 406 that are external to and not under the control of the owner or operator of the record manager device 402, the translation module 416 of the record manager device 402 may not be able to change the contents of the records 410. Therefore, the translation module 416 can create a memory structure that associates different parts of the demographic information in the different records 410 to allow for the record manager device 402 to more quickly determine whether records 410 match each other at a later time. Alternatively, the translation module 416 can change or add to the demographic information in one or more of the records 410 to make later matching of patient records 410 a faster task. For example, the data manager device 402 may have the ability to change or add to at least some of the patient records 410 and can correct typographical errors, data entry errors, or the like, or can add demographic information to a record 410 to more easily determine that this record 410 matches another record 410 from the same or another data source 404, 406.

Figure 9:
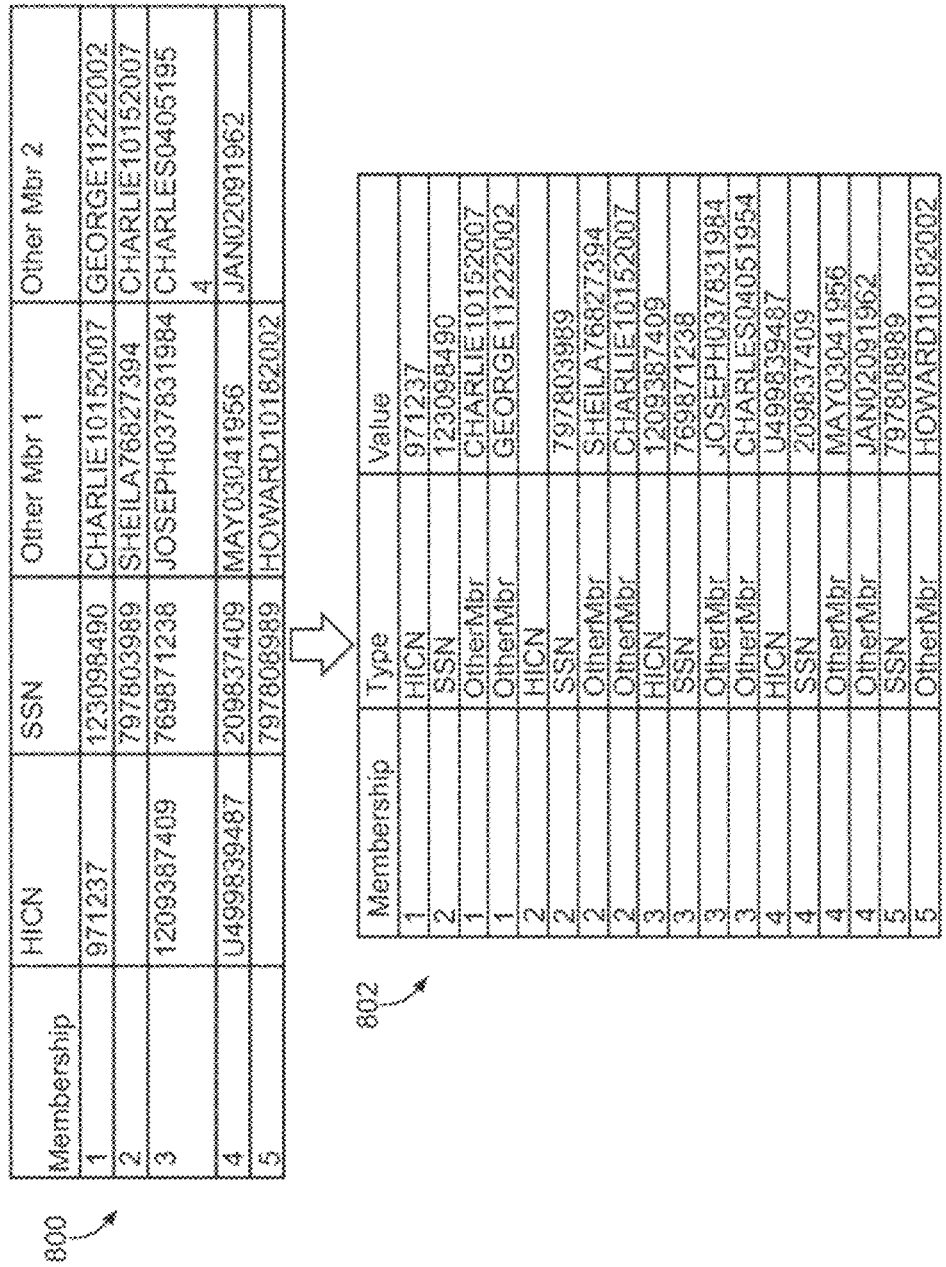
FIG. 9 illustrates one example of how the translation module can organize the demographic information in several records for faster comparison to identify similarities or differences between the records.

FIG. 9 illustrates one example of how the translation module 416 can organize the demographic information in several records 410 for faster comparison to identify similarities or differences between the records 410. A first table 800 represents the demographic data included in each of several different records 410. The records 410 are individually identified as 1, 2, 3, 4, and 5 beneath the column header "Membership." As shown, each record 410 includes demographic information in two or more categories. These categories are shown as the column headers "HICN" (representing a Medicare beneficiary number), "SSN" (representing social security numbers), "Other Mbr 1" (representing other demographic information, such as first names, birth dates, or a combination thereof), and "Other Mbr 2" (representing other demographic information, such as first names, birth dates, or a combination thereof). Comparing the sets of demographic information associated with the different records 410 with each other while these sets of demographic information remain separate can be a time-intensive process.

The translation module 416 can re-organize the demographic information into another format in the database 418, such as by creating another table 802 that organizes the demographic data from the different records 410 numbered 1, 2, 3, 4, and 5 as shown in FIG. 9. This table 802 organizes each of the connecting data elements in the records 410 (e.g., Medicare beneficiary number, social security number, first names and birth dates, etc.) into a name and value. For example, each element of the demographic information in a record 410 may be separately associated with an identification of the record 410 (e.g., under the "Membership" column header in the table 802), the corresponding name or category of the demographic information (e.g., under the "Type" column header in the table 802), and the corresponding value of the demographic information (e.g., under the "Value" column header in the table 802). This re-organized demographic information can be more easily compared with each other to determine whether any records 410 are associated with the same household and/or are associated with the same person.

For example, the record manager device 402 can then perform a database join of the table 802 to see whether any combinations (e.g., rows) of the category of demographic information (e.g., "Type") and the corresponding information (e.g., "Value") satisfy the matching rules 412 described above. In the illustrated example, records 1 and 2 would be demonstrated as the same household on the basis of an additional family member, while records 3 and 4 would be demonstrated as the same household on the basis of the strings 209837409 and 209387409, which have a two-character transposition in the social security number. The record manager device 402 can then perform an additional database join to find connections to connections. Stated differently, the record manager device 402 can then use the previously discovered household connections between the records 1 and 2 and between the records 3 and 4. The record manager device 402 can then determine that record 5 shares the same household as record 1 due to the fact that records 2 and 5 share a household (on the basis of an eight-character nonconsecutive match in the social security number in the records 2 and 5).

In one embodiment, a person associated with one or more records 410 that are identified as being associated with that person can provide feedback regarding this association. This feedback can be an affirmation that the record(s) 410 identified as representing that person do, in fact, belong to that person or a denial that the record(s) 410 represent that person. The person may determine that one or more records 410 identified by the record manager device 402 as representing that person do not represent that person. The person can provide an affirmation or denial of the identification and provide this affirmation or denial to the record manager device 402 via a patient interface device 428. The patient interface device 428 can be one or more computerized devices used by a patient to provide this affirmation or denial feedback. Examples of the patient interface device 428 include a mobile telephone, a personal digital assistant, a computing system, a mobile electronic device, a desktop computing device, a notebook computing device, a netbook computing device, or the like.

The record manager device 402 can use this feedback to assist with later determinations of whether records 410 are or are not associated with that person. For example, first and second records 410 can be identified by the record manager device 402 as being representative of a patient. If that patient indicates that the second record 410 is not representative of the patient, then the record manager device 402 can store this feedback in the database 418. During subsequent examinations of the records 410, the record manager device 402 can use this denial as an additional item of information that is used to prevent the second record 410 from being associated with that same patient and to prevent other records 410 from being associated with that patient (by way of being linked to the second record 410).

As another example, a third record 410 can be identified by the record manager device 402 as not being representative of a patient. If that patient indicates that the third record 410 is representative of the patient, then the record manager device 402 can store this feedback in the database 418. During subsequent examinations of the records 410, the record manager device 402 can use this feedback as an additional item of information that is used to link the first and third records 410, as well as records linked to the patient via the third record 410, as being associated with that patient.

Figure 10:
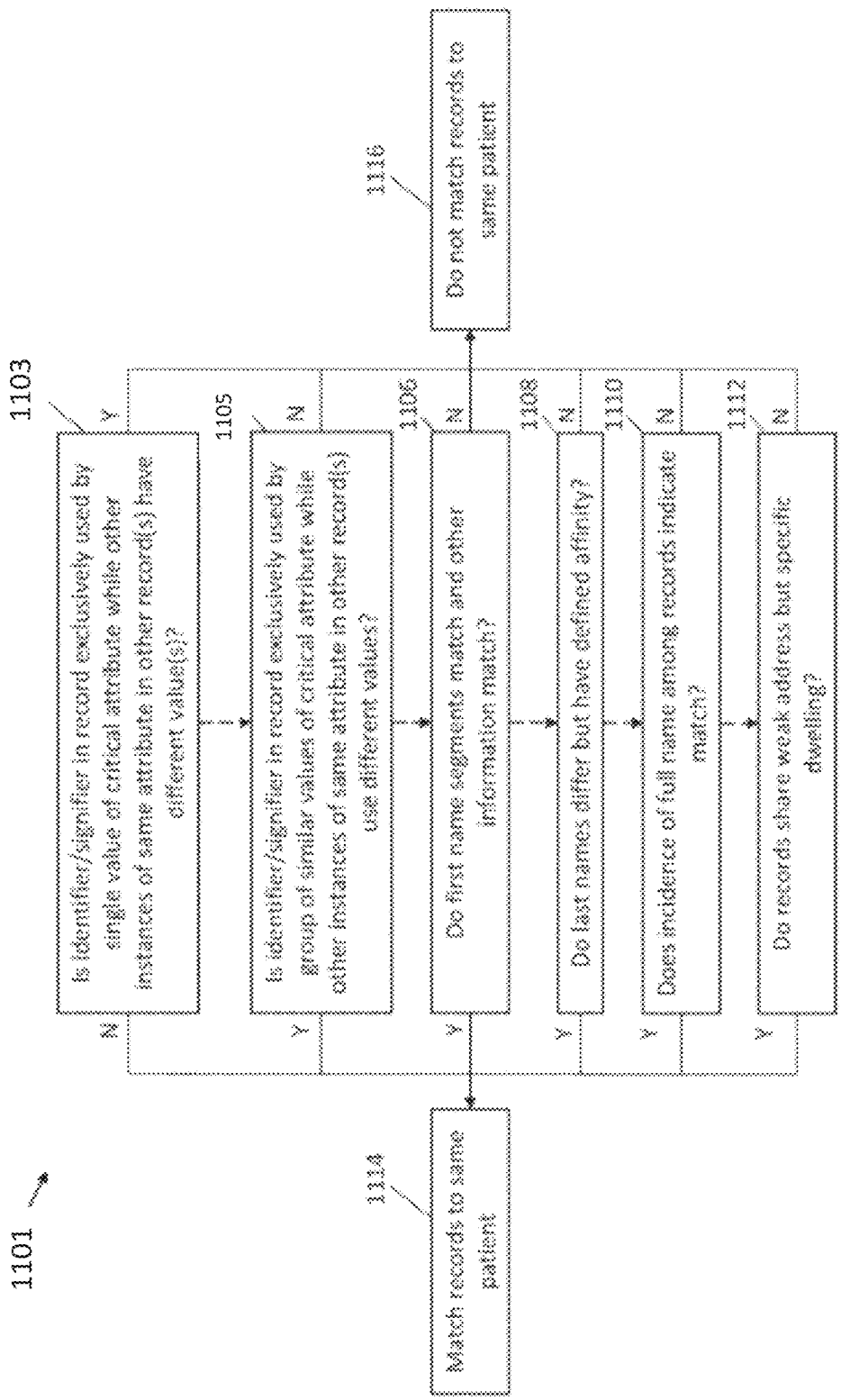
FIG. 10 illustrates a flowchart of one embodiment of a method for determining whether patient records match each other.

FIG. 10 illustrates a flowchart of one embodiment of a method 1101 for determining whether patient records 410 match each other. The method 1101 can represent operations performed by the record manager device 402 to determine whether multiple patient records 410 belong to or are otherwise associated with the same person. This method 1101 can be performed in addition to or as an alternate to the method 500 to determine whether two or more records 410 belong to or are otherwise associated with the same person (e.g., include medical information and/or private health information for the same person). The flowchart of the method 1101 includes several rules or criteria 1103, 1105, 1107, 1108, 1110, 1112 that can be applied in an individual, group, or sequential manner against the information contained in two or more of the records 410 to determine whether these records 410 belong to or are otherwise associated with the same person. For example, two or more records 410 may be examined by sequentially moving through a group of some or all of the rules or criteria 1103, 1105, 1107, 1108, 1110, 1112 in the order shown in FIG. 10 or in another order. Alternatively, one or more (or each) of the rules or criteria 1103, 1105, 1107, 1108, 1110, 1112 can be applied to the records 410 being examined until the records 410 match or satisfy one of the rules (at which point the records 410 are determined to belong to the same patient). This can result in fewer than all of the rules or criteria 1103, 1105, 1107, 1108, 1110, 1112 being used to determine whether the records 410 belong to the same person (e.g., where the records 410 satisfy one of the rules or criteria 1103, 1105, 1107, 1108, 1110, 1112 before one or more other rules or criteria 1103, 1105, 1107, 1108, 1110, 1112 are considered). The rules or criteria 1103, 1105, 1107,

1108, 1110, 1112 can be used in addition to or in place of the rules or criteria set forth elsewhere herein.

At 1103, a single exclusivity rule or criterion is applied to the records 410 being considered for matching to the same person. This rule or criterion examines whether a particular or designated identifier or signifier in these records 410 is exclusively used by a single value of a designated attribute, while other designated instances of the same designated attribute have a different value. The identifier can be a unique number or alphanumeric string that is assigned to a person, such as a social security number, a member number, a beneficiary number (e.g., HICN), intra-family ordinal number, or the like. The identifier can be assigned by a healthcare provider, government agency, or the like. The identifier may not include demographic information, such as a name, age or age range, gender, marital status, number of children or dependents, etc. The signifier can be another identifier of the person. The designated attribute can be referred to as a critical attribute, and can include names, dates or birth, or the like. The attributes can be demographic or characteristics of a patient, such as a name, age or age range, gender, marital status, number of children or dependents, etc.

In applying this rule to the records 410, if the designated identifier (e.g., social security number, member number, HICN, etc.) or signifier is exclusively used by a single value of the designated attribute (e.g., name or date of birth), but other designated or critical instances of that attribute use a different value, then these differing values of the attributes may indicate that the records 410 do not belong to the same patient. As a result, flow of the method 1100 can proceed toward 1114 (where the records 410 are determined to not belong to the same person), can proceed to another rule or criterion (e.g., one or more of 1105, 1107, 1108, 1110, and/or 1112), or can terminate (as the records 410 already are determined to not match so further analysis may not be needed).

Conversely, if the designated identifier or signifier is exclusively used by a single value of the designated attribute and other designated or critical instances of that attribute use the same value, then these same attribute values may indicate that the records 410 do belong to the same patient. As a result, flow of the method 1100 can proceed toward 1116 (where the records 410 are determined to belong to the same person), can proceed to another rule or criterion (e.g., one or more of 1105, 1107, 1108, 1110, and/or 1112), or can terminate (as the records 410 already are determined to match so further analysis may not be needed). With respect to proceeding to another rule or criteria, in one embodiment, one or more additional rules or criteria may be used to confirm that the records do, in fact, belong to the same person.

At 1105, a group exclusivity rule or criterion is applied to the records 410 being considered for matching to the same person. This rule or criterion examines whether the particular or designated identifier or signifier in these records 410 is exclusively used by a group of values of designated attributes, while other designated instances of the same designated attributes have a different value. In applying this rule to the records 410, if the designated identifier (e.g., social security number, member number, HICN, etc.) or signifier is exclusively used by several similar values (e.g., two or more values) of the designated attribute, while other instances of that attribute use a different value, then these differing values of the attributes may indicate that the records 410 do belong to the same patient. This is in contrast to the single exclusivity rule or criterion of 1103, where these differing values indicate that the records 410 belong to different people. Flow of the method 1100 can proceed toward 1116 (where the records 410 are determined to belong to the same person), can proceed to another rule or criterion (e.g., one or more of 1105, 1107, 1108, 1110, and/or 1112), or can terminate (as the records 410 already are determined to match so further analysis may not be needed). With respect to proceeding to another rule or criteria, in one embodiment, one or more additional rules or criteria may be used to confirm that the records do, in fact, belong to the same person.

Alternatively, if the designated identifier or signifier is not used exclusively by the group of attributes (e.g., two or more of these attributes have different identifiers or signifier values), then a decision can be made that the records 410 do not belong to the same person (but likely belong to different people). Flow of the method 1100 can proceed toward 1116 (where the records 410 are determined to not belong to the same person), can proceed to another rule or criterion (e.g., one or more of 1105, 1107, 1108, 1110, and/or 1112) to see if the records 410 match according to another rule or criteria, or can terminate (as the records 410 already are determined to not match so further analysis may not be needed).

At 1107, first name segments in the records 410 are examined to decide whether the records 410 belong to the same person or different persons. This rule or criterion examines whether a designated segment of first names in the records 410 is the same. The rule or criterion may be satisfied (thereby determining that the records 410 belong to the same person) when at least a designated number of characters (e.g., the designated segment) of the first name in each of the records 410 being compared is the same. For example, if at least the first three characters in the first names in the records 410, the first letter of the first name in one record 410 and a first name initial in another record 410, the first nine letters in the first names in the records 410, etc., are the same, then the records 410 may be found to belong to the same person. In one example, this rule or criteria may be satisfied when the designated segment of the first names match, and one or more other mitigating factors exist. These mitigating factors can be a match between other names (e.g., last names), street addresses, postal codes, birth dates, or the like. Flow of the method 1100 can then proceed toward 1114 where the records 410 are determined to belong to the same person.

But, if at least the designated segment of characters in the first names in the records 410 do not match (and/or the other mitigating factors do not exist or are not present), then the records 410 may not be found to belong to the same person. Flow of the method 1100 can proceed toward 1116 (where the records 410 are determined to not belong to the same person), can proceed to another rule or criterion (e.g., one or more of 1105, 1107, 1108, 1110, and/or 1112) to see if the records 410 match according to another rule or criteria, or can terminate (as the records 410 already are determined to not match so further analysis may not be needed).

At 1108, last names in the records 410 are compared to decide whether the records 410 belong to the same person or different persons. This rule or criterion examines whether the last names in the records 410 differ, but the records 410 have a designated affinity. The designated affinity may be similarities or matches between the last names. For example, one designated affinity between the last names in the records may be found to exist where the last names differ by no more than a designated edit distance. Another designated affinity between the last names in the records 410 may exist where the last names have at least a minimum number of consecutive characters in the last names that are the same (not including blanks or spaces). Another designated affinity between the last names in the records 410 may exist where the last names match after honorifics are removed from the analysis (titles such as Ms., Mrs., Mr., Dr., etc. are not used in the comparison or are otherwise ignored in the analysis). The rule or criterion can be satisfied and the records 410 determined to belong to the same person where the records 410 include different last names but have at least the designated affinity. Flow of the method 1100 can then proceed toward 1114 where the records 410 are determined to belong to the same person.

But, if the last names differ and do not have at least a designated affinity, then the records 410 may not be found to belong to the same person. Flow of the method 1100 can proceed toward 1116 (where the records 410 are determined to not belong to the same person), can proceed to another rule or criterion (e.g., one or more of 1105, 1107, 1108, 1110, and/or 1112) to see if the records 410 match according to another rule or criteria, or can terminate (as the records 410 already are determined to not match so further analysis may not be needed).

At 1110, the incidences of names in the records 410 are compared and examined relative to a population to determine whether the records 410 belong to the same person. The first and last names in the records 410 can be compared with each other to determine if the first and last names in one record 410 match the first and last names in another record 410. If the first and last names match, then the incidences of a combination of the first name and the last name in the population is determined or obtained. The incidences of the combination of the first name and the last name can be a measurement, count, or other indication of how frequently the first name and last name are used together in a population, such as the population of a country (e.g., the United States). Some names (e.g., Mark Smith or Maria Rivera) may have greater incidences than other names (e.g., Brynhild Grasmoen) in the population.

The decision of whether records 410 having matching first and last names belong to the same person may depend on the frequency at which the first and last names appear in the population. Records 410 having matching common names (e.g., the same name) that appear more often in the population (e.g., Mark Smith) may be less likely to be found to belong to the same person than records 410 having matching uncommon names that appear less often in the population (e.g., Brynhild Grasmoen). In one embodiment, if the matching full name in the records 410 is used by fewer than a designated number of patients in a population (e.g. less than one hundred, less than twenty-five, less than five, etc.), then the records 410 can be found to belong to the same person. Flow of the method 1100 can then proceed toward 1114 where the records 410 are determined to belong to the same person.

But, if the full names match but are used by a large number of people in the population (e.g., more than the designated number), then the records 410 may not be found to belong to the same person. Flow of the method 1100 can proceed toward 1116 (where the records 410 are determined to not belong to the same person), can proceed to another rule or criterion (e.g., one or more of 1105, 1107, 1108, 1110, and/or 1112) to see if the records 410 match according to another rule or criteria, or can terminate (as the records 410 already are determined to not match so further analysis may not be needed).

At 1112, addresses included in the records 410 are examined to determine whether the records 410 belong to the same person. Some mailing addresses may be considered to be "weak" addresses where the addresses are more common than others. Street addresses that are used or appear more often in the population than a designated number or percentage may be considered weak addresses. Examples of weak addresses may include addresses that happen to be dormitories, long-term care facilities, prisons, large apartment buildings, etc. An address may be considered to be a weak address when the address appears in other records 410 or in the population more than a designated number of times and/or in more than a designated percentage of records 410 or the population.

If records 410 being compared have the same weak address, then the dwelling unit in the addresses may be compared to determine whether the records 410 belong to the same person. The dwelling unit can be the apartment number instead of a house number. For example, one record 410 may have an address of "113 S. First St., #313" and another record 410 may have an address of "113 S. First St., #112." While the street addresses (e.g., "First St.") may be weak, the dwelling units do not match. This can indicate that the records 410 do not belong to the same person. Flow of the method 1100 can proceed toward 1116 (where the records 410 are determined to not belong to the same person), can proceed to another rule or criterion (e.g., one or more of 1105, 1107, 1108, 1110, and/or 1112) to see if the records 410 match according to another rule or criteria, or can terminate (as the records 410 already are determined to not match so further analysis may not be needed).

But, if the dwelling units match (e.g., both records 410 have an address of "113 S. First St., #211"), then a decision can be made that the records 410 belong to the same person. Flow of the method 1100 can then proceed toward 1114 where the records 410 are determined to belong to the same person.

In addition to the problems with matching patient records identified above, the demographic information contained in one record may change over time while the demographic information contained in another record (for the same person or patient) remains the same or changes in a different way. For example, over the course of an extended treatment for a patient, the patient may move, change names (e.g., due to a change in marital status or otherwise), or the like. This changed information may be updated in one or more records of the patient, but not in one or more other records. This may occur where the records are provided or updated by different healthcare providers, but at different rates or frequencies. For example, over the course of several months or years, a patient may have a first record that is updated frequently (e.g., each month when the patient obtains a prescription refill) and another record that is updated infrequently (e.g., once a year at the patient's annual physical or checkup). If the demographic information of the patient changes during this time period, one record may be updated with the new or changed demographic information, while another record is not updated. This may occur where the patient changes addresses, changes names, or the like. The record that is updated more frequently may reflect this change sooner than the record that is updated less frequently.

But, both records may be used when making healthcare decisions, as described above. The change in demographic information appearing in one record, but not the other record, can result in the records not being matched to the same person. Accordingly, the records may be undermatched and one or more medical decisions may be made based on less than all of the relevant information, which can pose significant threats to the safety and health of the patient, as set forth above.

To address this issue, the record matching system can use patient experiences to infer, from a continuity of care, that the patient being served during a prolonged or extended treatment is the same patient at the end of the treatment even though one or more aspects of the demographic information associated with the patient in one or more records changes during the treatment. For example, pharmacy prescriptions can be refilled many times. The patient receiving the medication as of the first fill of the prescription must be or is very highly likely to be the same patient as of the last refill of the prescription, even though the patient may have changed name, address, and/or gender; changed (e.g., corrected) date of birth, social security number, or other identifying information. Consequently, the record matching system may have access to these repeated events related to or falling within an extended course of treatment, and may use these events or course of treatment to link or match records that otherwise may not be matched.

For example, the record matching system may determine that first and second records match to the same patient using one or more of the processes, techniques, or algorithms described herein. The record manager device can match the first and second records to the patient. The record manager device may record (e.g., in the memory) that the records are associated with the same person. Alternatively, one or both of these records may be updated to include information indicating that the records belong to the same person. The first record may include information indicating that the patient will be or is undergoing treatment. This information can be a unique identifier of a medical treatment, a unique identifier of a pharmacy that provided a medication prescribed for the medical treatment, a unique identifier (e.g., prescription number) of the medication that was provided by the pharmacy, etc. The medical treatment may or may not be an extended treatment (e.g., a course of treatment) extending over several weeks, months, years, or the like. This continued treatment may be identified by data in the first record indicating a medication prescription having many refills over an extended period of time (e.g., several weeks or months), a prescription for therapy lasting over the extended period of time, or other medical treatments to occur or recur over the extended period of time.

The first and second record may be linked with each other based on the identifying information related to the treatment or medication. For example, a unique identifier in the first record may be connected or linked with a first patient address. This same unique identifier may be connected or linked with a different, second patient address in the second record. The connection of the unique identifier with the different first and second patient addresses in the different first and second records may be used by the record manager device to determine that the first and second addresses are associated with the same household (e.g., the first address or the second address may be an old address that has not yet been updated in the corresponding record). This connection or link can be used to determine that the first and second records do match the same patient.

Either the first record or the second record may be modified based on a change in one or more circumstances of the patient using this discovered connection or link. As described above, the patient may change or correct names, address, gender, or other demographic information during the course of treatment. But the healthcare provider(s) involved in providing the course of treatment may only update one of the two (or several more) records associated with the patient (and previously matched to each other and the patient). Subsequent examinations of the records by the record manager device may result in the record manager device determining an undermatch between the records. For example, the differing demographic information between the records may result in the record manager device determining that the records do not belong to the same person.

The record manager device can use the information stored in the memory and/or in one or more of the records to determine that the person undergoing the treatment having a unique identifier is associated with both or all of these records, regardless of the different demographic information in the records. For example, even though one or more records may not have the most up-to-date or accurate demographic information, the record manager device can determine that these records still match to the same patient due to the unique identifier associated with the same treatment.

Even with the patient record matching system 400 and the methods 500, 600, 700, 1100 shown in FIGS. 5, 7A, 7B, 8, and 10, some records may still be undermatched to patients. That is, some records may not be matched to the correct patient. For example, the methods 500, 600, 700, 1100 described above can result in more potential undermatched patients than the patient record matching system 400 can process at once. This can be especially problematic when the matching processes of the methods 500, 600, 700, 1100 are first performed on a set of patient records. As a result, if a group of undermatched records is found, there are likely to be times that some or most of the cache cannot be addressed or corrected and must be delayed for processing until a later time. This problem is compounded by the volatility of patient demographics. A potential undermatch for a patient record may be found, introduced to the patient record matching system for correction, and left unchanged because there is insufficient evidence to join that patient record with another patient record. But additional data may be received later that allows greater confidence that the records belong to the same patient. As a result, the patient record matching system may need to repeatedly check for undermatching of patient records when new demographic data about a patient is received.

The patient record matching system may need to prioritize which undermatched patient records to correct when there is a backlog of potential undermatched records. This prioritization may be based on a likelihood that the patient will be served while there is relevant information missing. For example, the patient records having patient identifiers used more recently and/or more frequently may have a higher priority for examining those records to determine and rectify undermatching. Additionally, if the computer processing capacity to correct the patient records is dependent on the size of each record, patients at equal risk who have larger records can be de-prioritized in favor of patients with smaller records so that more risks can be mitigated more quickly.

When there is a backlog of potential undermatched patient records, certain candidate records may be prioritized for correction, yet left unchanged because there is insufficient evidence to join records. To prevent unnecessary re-processing of such candidate records, the patient record matching system can recognize that the system already has examined those records and avoid re-processing those records until there is new evidence which might cause a different patient matching decision.

To meet these goals, the patient record matching system can, on a regular basis (e.g., periodically or otherwise matching the capacity of the patient record matching system for correcting patient records) find candidate records that satisfy an undermatch search algorithm. The system can then identify the date on which each candidate record that satisfied the undermatch search algorithm last had demographic information changed, as well as the date on which less recently used patient identifiers in the records last had activity (e.g., were last used to process a claim for benefits under the pharmacy benefit plan).

The patient record matching system can then prioritize (for correction) the candidate records that were not previously considered for correction by the patient record matching system after the most recent change in demographic information in the records and that have the most recent activity (e.g., for processing benefit claims under the pharmacy benefit plan) under the less recently used patient identifier. Records that were previously considered for correction after a recent change in demographic information or that do not have as recent activity with the less recently used patient identifier do not have priority over other records (e.g., for correction).

A correction engine (e.g., the record manager device 402) can have capacity constraints for correcting records. For example, the correction engine may only be able to correct a designated number of records and/or data size of the records per unit time (e.g., per hour, per day, etc.). The correction engine may receive up to as many of these prioritized records for correction as the capacity of the correction engine allows. The records can then be corrected (e.g., the data in the records modified) so that the records are correctly matched with other records associated with the same patient. Other records that were not sent to or corrected by the correction engine can be recorded or labeled with data indicating that the records were considered for correction but left unchanged, along with the date on which the records were considered for correction but left unchanged.

Figure 11:
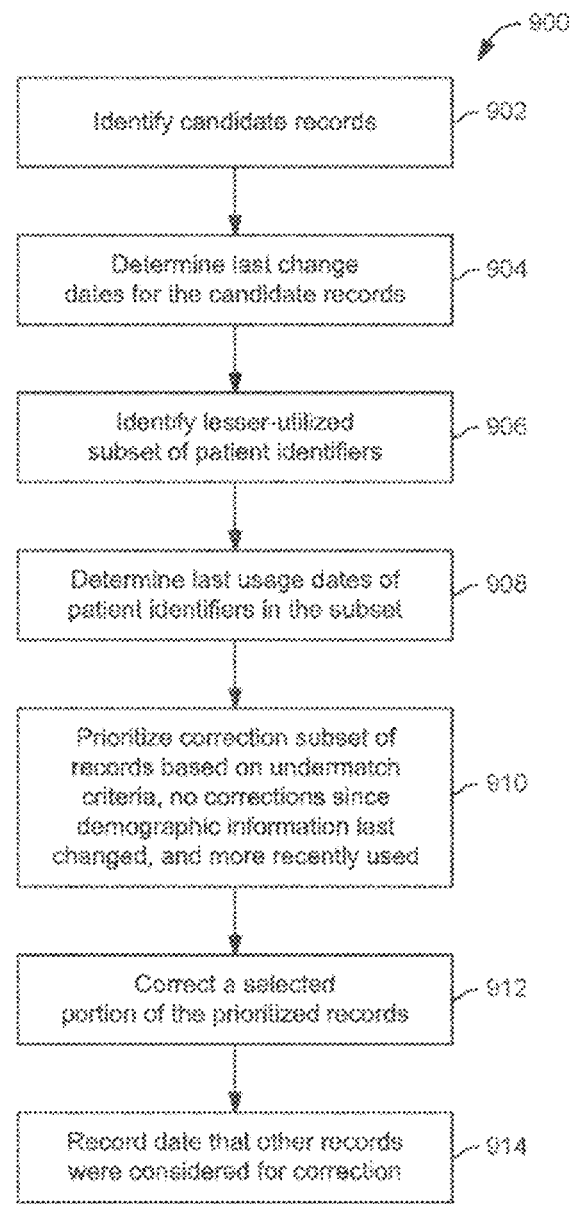
FIG. 11 illustrates a flowchart of a method for correcting undermatched patient records.

FIG. 11 illustrates a flowchart of a method 900 for correcting undermatched patient records. The method 900 can represent operations performed by the patient record matching system 400 to match records with patients by correcting errors in the records (or by matching the records with the patients without changing any contents of the records) and reduce the quantity of undermatched patient records.

At 902, patient records are examined to identify candidates for undermatching. The patient records can be examined by determining which records are potentially undermatched to patients. These records can be referred to as candidate records. The candidate records can be identified by determining which of the patient records match or satisfy one or more undermatch criteria. These criteria can be used to identify or select combinations of patient records that are likely or most likely to be associated with or representative of the same patient. Patient records having information that does not match or meet the criteria may be less likely to be associated with or representative of the same patient.

As one example of undermatch criteria, the membership identifiers of the records in the pharmacy benefit plan can be examined to identify which candidate records satisfy the criteria. The membership identifier can be a member number of a patient within the pharmacy benefit plan and may be the identifying information provided to a pharmacy or other healthcare provider to obtain benefits under the plan. The patient records having a combination of (a) the same membership identifier in the pharmacy benefit plan and (b) the same patient name, and that have multiple instances of different patient identifiers and either a single person number or a birth date gap that is less than a designated length of time can match or satisfy the undermatch criteria (and therefore be identified as candidate records for correction). The single person number can indicate that the patient(s) associated with the records is or are not married. The birth date gap can be the length of time between the oldest and most recent birth dates that appear in the patient records being examined as being undermatched to the same patient. For example, one record may include a birth date of 15 Nov. 1976 and another record may include a birth date of 15 Nov. 1967, thus having a birth date gap of nine years. As another example, one record may include a birth date of 15 Nov. 1976 and another record may include a birth date of 15 Jan. 1976, thus having a birth date gap of ten months. The designated length of time is 367 days in one embodiment but may be a shorter length of time.

Another example of undermatch criteria may be based on membership identifiers, the birth dates (e.g., the month, date, and year of birth as opposed to just the year of birth), the patient identifiers, and the patient names. This criteria can be met or satisfied for those records having the same membership identifier and the same date of birth as candidate records, where those records have the edit distance between patient names of no more than a first designated threshold and multiple instances of different patient identifiers. This first designated threshold can be one in one example, but optionally may be a larger number. For example, patient records having the same membership identifiers and the same date of birth but having patient first names having an edit distance of no more than one and multiple, different patient identifiers can be identified as candidate records.

Another example of undermatch criteria that may be based on the membership identifier, the birth years (e.g., the year of birth, but not necessarily the month or date), the patient identifiers, and the patient names. This criteria can be met or satisfied for those records having the same membership identifier and the same birth year as candidate records, where those records also have patient first names that are designated nicknames of each other and that have multiple, different patient identifiers. The record manager device 402 can store a list, table, or the like, of combinations of names that are designated nicknames of each other (e.g., Christopher and Chris; Richard and Dick; Margaret and Peggy; Jackson and Jack; etc.). This list, table, or the like can be referenced to determine whether a patient name (e.g., a patient first name) in different records are designated nicknames of each other, such as where one record uses Jackson and another record uses Jack.

The undermatch criteria also can be based on part, but not all, of the membership numbers. For example, an undermatch criteria can be based on partial membership numbers, the patient names, the patient identifiers, and the birth years. The criteria can be met or satisfied by the records having at least a designated portion of membership numbers that are the same, the same birth year, patient last names having an edit distance of no more than the first designated threshold, a designated string portion of the patient last names matching each other, the patient names being designated nicknames, and multiple, different patient identifiers can be selected as candidate records. The designated portion of the membership numbers can be eight characters in one embodiment, but optionally may be a larger or smaller number of characters. This portion of the membership numbers can occur at the beginning, middle, or end of the membership numbers. The designated string portion of the patient last names can be the first three characters of the patient last names, or a shorter or longer portion. Therefore, in one example, records having membership numbers of AWB123456789 and AWB223456789, the same year of birth, patient last names of Decatorsmith and Dectorsmith, patient first names of John and Jon (designated nicknames of each other), and multiple, different patient identifiers can be selected as candidate records.

As another example, an undermatch criteria can be met or satisfied when records have any combination of nonspace characters in a string of at least a designated length in the membership numbers and dates of birth, as well as an edit distance between patient names that is no more than the first designated threshold and multiple, different patient identifiers. The designated length of the string of nonspace characters can be eight in one embodiment, but optionally may be a longer or shorter string of characters.

The undermatch criteria optionally can be based on addresses in the patient records. For example, the criteria can be met or satisfied by the patient records having the same street in the addresses in the records, the same zip codes, and the same birth years, where the patient names in the records are the same, are designated nicknames, or have an edit distance of no more than the first designated threshold, and where there are multiple, different patient identifiers. These records may be selected as candidate records for correction. As another example, patient records having the same street in the addresses, the same zip code, and the same patient first name in which the birth dates in the records are no further apart than a designated time period and there are multiple instances of different patient identifiers may be selected as candidate records. As described above, the designated time period can be 367 days or a shorter or longer time period.

Optionally, other identifiers of households in patient records can be used to determine which records are candidates for correction. As one example, the undermatch criteria can identify patient records as candidate records where the patient records have the same membership identifier or number, a non-default entry for another unique identifier, and the same birth date, where there are multiple, different patient first names in the records (but with the first and last patient names transposed or switched in locations in the records) and there are multiple instances of different patient identifiers. The unique identifier can be a government-issued identifier, such as social security number, a Medicare beneficiary identifier, or another unique number provided to a patient. The non-default entry can be any entry that is not the default or standard entry provided in a patient record when the number is not known. For example, some patient records may include entries of "null," or "000-00-000," etc. when the patient social security number is not known.

In another example, patient records may satisfy the undermatching criteria and be identified as candidate records when the patient records include the same membership identifier or number, the same government-issued identifier number (e.g., the same social security number or the same Medicare beneficiary number) and have the same date of birth, where the records have multiple instances of different patient identifiers and the same first name of the patient or different first names of the patient with an edit distance that is no greater than the first designated threshold described above.

Optionally, the undermatch criteria can be met by patient records having at least a designated number of characters in an identifier number, such as a government-issued identifier number (e.g., Medicare beneficiary identifier numbers), with multiple, different first names of patients having an edit distance that is less than a second designated threshold. The designated number of characters can be eight characters, but alternatively may be a larger or smaller number of characters. The second designated threshold can be three in one embodiment, but optionally can be a smaller or larger number. Combinations of patient records meeting these criteria can be identified as As another example, patient records having the same government-issued identifier numbers that do not begin with a designated default sequence (e.g., 0000, spaces, asterisks, etc.) but that are associated with the same benefit group, having patient first names that begin with the same letter, and have multiple instances of different patient identifiers may be selected as candidate records. The benefit group can be Medicare part D or another group of Medicare.

The criteria also can be based on combinations of patient names and dates of birth appearing in the patient records. For example, the patient records having the same patient first name, the same patient last names, the same birth dates, the same government-issued identifier (e.g., social security number) that is not a default value, no more than one non-default other government-issued identifier (e.g., Medicare beneficiary number), and no membership in a pharmacy benefit plan that is a discount card membership can be identified as candidate records.

Another example of the undermatch criteria can be met or satisfied by patient records having different patient names (e.g., different first names), different dates of birth, and two or more of the same membership identifiers in the pharmacy benefit plan and have more than two different patient identifiers between the patients. For example, a first patient record having a patient first name of Bill, a birth date of 2 Feb. 1991, a first membership number X123, a second membership number Q345, and two different patient identifiers, and a second patient record having a different patient first name of Cal, a different birth date of 5 Mar. 1997, and both the same first and second membership numbers may be selected as candidate records for correction.

At 904, last change dates are determined for the candidate records. The last change dates indicate when demographic information within the candidate records was last changed. For example, the last change date of a candidate record can be the most recent date that any demographic information in the candidate record was modified, removed, or added.

At 906, a lesser-utilized subset of the patient identifiers is identified. This subset can include the patient identifiers that have been used less than one or more other patient identifiers among the candidate records being examined. For example, the lesser-utilized subset can include the patient identifiers in the candidate records that have been associated with fewer claims for benefits under the pharmacy benefit plan than 90% of other patient identifiers in the candidate records. Stated differently, the lesser-utilized subset can be those records associated with patient identifiers that are used less than 90% of other patient identifiers in the candidate records. The 90% threshold is provided merely as one example. Alternatively, the lesser-utilized subset can be formed of those patient identifiers used less than 95% of the patient identifiers in the candidate records, less than 80% of the patient identifiers in the candidate records, less than 70% of the patient identifiers in the candidate records, or the like.

At 908, last usage dates for the lesser-utilized subset of the patient identifiers are determined. The last usage dates can be the most recent date for each of the patient identifiers in the lesser-utilized subset that the patient identifier was used to process a claim for benefits under the pharmacy benefit plan (as determined from 904). At 910, a correction subset of the candidate records is prioritized for correction. This correction subset can include those candidate records that satisfy the one or more undermatch criteria (determined at 902), that were not corrected since the last change date when the demographic information within the candidate records was last changed, and that have one or more of the patient identifiers within the lesser-utilized subset and that have more recent dates of the last usage dates than others of the patient identifiers within the lesser-utilized subset. This correction subset of the candidate records is less than all of the candidate records in one embodiment.

At 912, a portion of the correction subset of the candidate records is supplied to the correction engine for correction of the candidate records. The portion of the correction subset of candidate records is selected based on the prioritization of the candidate records in the correction subset (determined at 910) of the candidate records and a capacity constraint of the correction engine. For example, a subset of these records can be sent to the correction engine based on (a) the priority of the candidate records and (b) the number of candidate records and/or the size of the data in the candidate records that can be corrected within the capacity of the correction engine. The records can be corrected by changing data included in the records. For example, the demographic information in one or more of the candidate records can be changed to match another candidate record so that these records are associated or matched with each other. This can ensure that all records associated with the same patient are more easily obtained by healthcare providers, pharmacy benefit managers, or the like, for benefit plan decisions and/or healthcare decisions.

At 914, for the candidate records that were not sent to the correction engine for correction, the date that these records were considered for correction can be recorded. For example, information on when the candidate records were considered for correction but not corrected can be added to the candidate records or stored in another memory. This information can be later used to prioritize the records for correction, as described above at 910.

Figure 12:
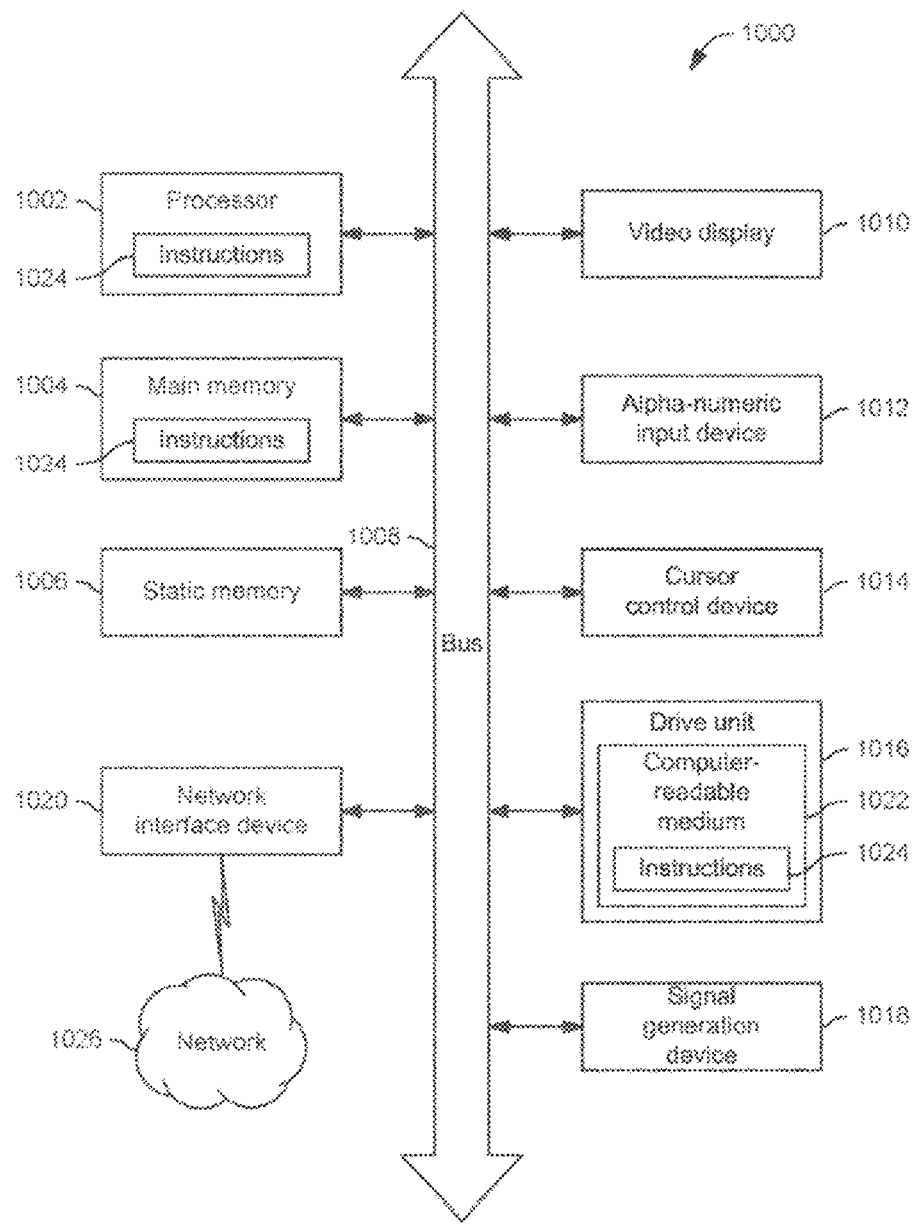
FIG. 12 shows a block diagram of a computer system within which a set of instructions may be executed causing the machine to perform any one or more than one methods, processes, operations, or methodologies discussed herein.

FIG. 12 shows a block diagram of a computer system 1000 within which a set of instructions may be executed causing the machine to perform any one or more than one methods, processes, operations, or methodologies discussed herein. For example, the system 1000 may compare demographic information in records 410 to determine which records 410 are associated with the same household and which of the records 410 that are associated with the same household belong to the same person. The devices 1006-1030, for example, may include the functionality of the one or more than one computer systems 1000. These devices and systems are dedicated to performing any one or more than one methods, processes, operations, or methodologies discussed herein.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The example computer system 1000 includes a processor 1002 (e.g., a central processing unit (CPU), a graphics processing unit (GPU) or both, etc.), a main memory 1004 and a static memory 1006, which communicate with each other via a bus 1008. The computer system 1000 further includes a video display unit 1010 (e.g., a liquid crystal display (LCD) or a cathode ray tube (CRT), etc.). The computer system 1000 also includes an alphanumeric input device 1012 (e.g., a keyboard, etc.), a cursor control device 1014 (e.g., a mouse, etc.), a drive unit 1016, a signal generation device 1018 (e.g., a speaker, etc.) and a network interface device 1020.

The drive unit 1016 includes a computer readable medium 1022 on which is stored one or more than one sets of instructions 1024 (e.g., software, etc.) embodying any one or more than one methodologies or functions described herein. The instructions 1024 may also reside, completely or at least partially, within the main memory 1004 and/or within the processor 1002 during execution thereof by the computer system 1000, the main memory 1004 and the processor 1002 also constituting non-transitory computer readable media. When loaded with the instructions 1024, the processor 1002 is a machine dedicated to only the present processes and methodologies.

The instructions 1024 may further be transmitted or received over a network 1026 via the network interface device 1020. The network 1026 can represent the network 104 shown in FIG. 1.

While the computer-readable medium 1022 is shown in an example embodiment to be a single medium, the term "computer-readable medium" should be taken to include a single medium or multiple media (e.g., a centralized or distributed database, and/or associated caches and servers, etc.) that store the one or more than one sets of instructions. The term "computer-readable medium" shall also be taken to include any medium that is capable of storing or encoding a set of instructions for execution by the machine and that cause the machine to perform any one or more than one methodologies of the present disclosure. The term "computer-readable medium" shall accordingly be taken to include, but not be limited to, solid-state memories, and optical media, and magnetic media. In some embodiments, the computer-readable medium is a non-transitory computer-readable medium. In other examples, a computer-readable medium is any medium that satisfies statutory requirements and stores instructions for use by a machine.

Figure 13:
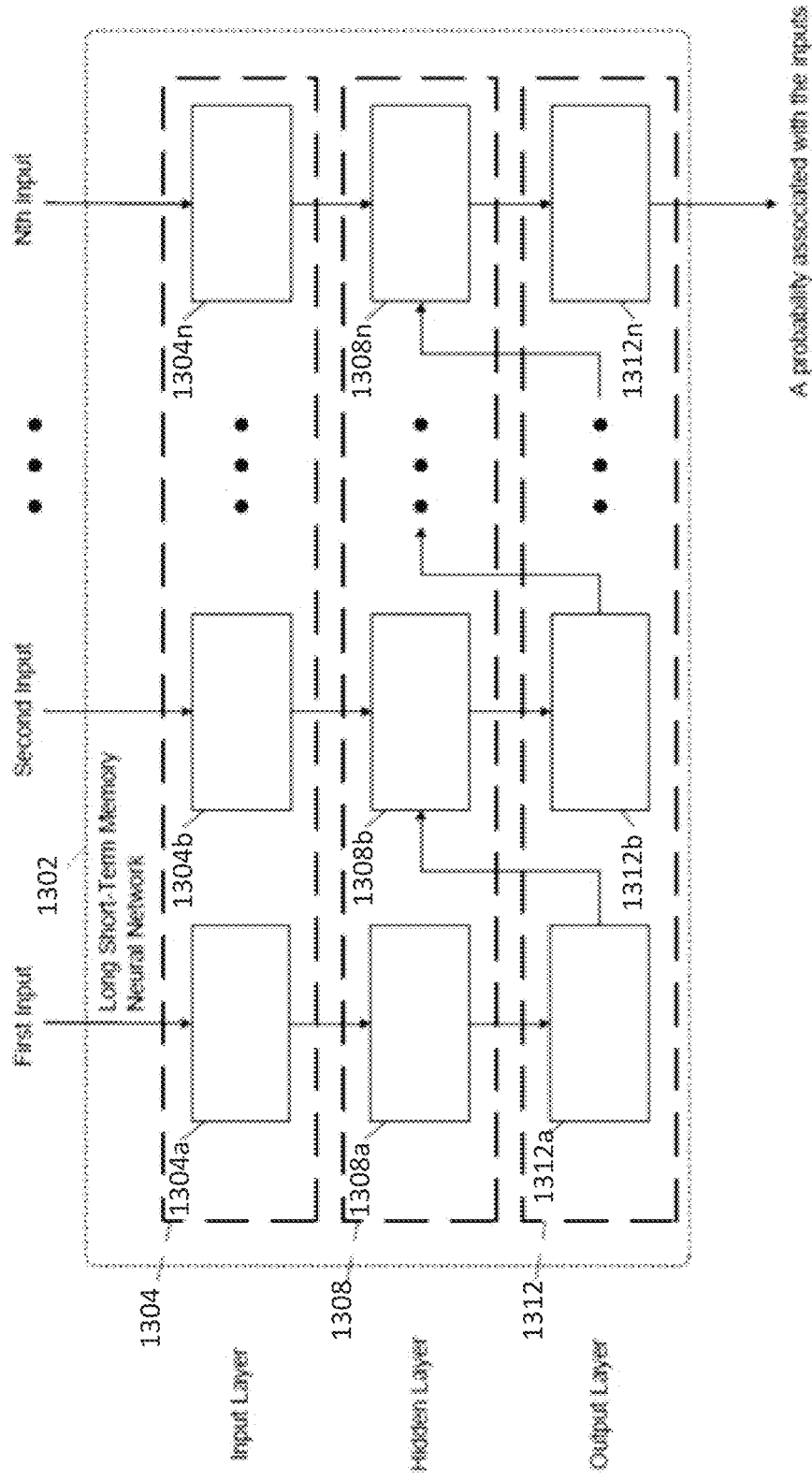
FIG. 13 illustrates a functional block diagram of an example neural network that can be used by the record manager device for matching records with the same person.

As previously stated, one or more of the record matching systems described herein may be implemented in an AI or machine-learning system. FIG. 13 illustrates a functional block diagram of an example neural network 1302 that can be used by the record manager device for matching records with the same person as described herein. In an example, the neural network 1302 can represent a long short-term memory (LSTM) neural network. In an example, the neural network 1302 can represent one or more recurrent neural networks (RNN). The neural network 1302 may be used to implement the machine learning as described herein, and various implementations may use other types of machine learning networks. The neural network 1302 includes an input layer 1304, one or more intermediate or hidden layers 1308, and an output layer 1312. Each layer 1304, 1308, 1312 includes artificial individual units, or neurons. Each neuron can receive information (e.g., as input into the neural network 1302 or as received as output from another neuron in another layer or the same layer), process this information to generate output, and provide the output to another neuron or as output of the neural network 1302. The input layer 1304 may include several input neurons 1304a, 1304b . . . 1304n, the hidden layer 1308 may include several intermediate neurons 1308a, 1308b . . . 1308n, and the output layer 1312 may include several output neurons outputs 1312a, 1312b . . . 1312n. The inputs may include, for example, patient records, parts of patient records, or the like.

Each neuron can receive an input from another neuron and output a value to the corresponding output to another neuron (e.g., in the output layer 1312 or another layer). For example, the intermediate neuron 1308*a* can receive an input from the input neuron 1304*a* and output a value to the output neuron 1312*a*. Each neuron may receive an output of a previous neuron as an input. For example, the intermediate neuron 1308*b* may receive input from the input neuron 1304*b* and the output neuron 1312*a*. The outputs of the neurons may be fed forward to another neuron in the same or different intermediate layer 1308.

The processing performed by the neurons may vary based on the neuron, but can include the application of the various rules or criteria described herein to partially or entirely decide whether two or more records match the same person or patient. The output of the application of the rule or criteria can be passed to another neuron as input to that neuron. One or more neurons in the intermediate and/or output layers 1308, 1312 can determine that the records match or do not match. The last output neuron 1312*n* in the output layer 1312 may output a matching or no-match decision. For example, the output from the neural network 1302 can be an indication that two (or more) records match a patient, or that two (or more) records do not match to the same patient. Alternatively, the output can be a probability indicating that the records do (or do not) match to the same patient. Although the input layer 1304, the intermediate layer(s) 1308, and the output layer 1312 are depicted as each including three artificial neurons, one or more of these layers may contain more or fewer artificial neurons. The neurons can include or apply one or more adjustable parameters, weights, rules, criteria, or the like, as described herein, to perform the processing by that neuron.

In various implementations, the layers of the neural network 1302 may include the same number of artificial neurons as each of the other layers of the neural network 1302. For example, historical patient data may be processed to provide information to the input neurons 1304*a*-1304*n*. The output of the neural network 1302 may represent a match or no match of the records to the same patient. More specifically, the inputs can include known facts stored in the patient records. The known facts can be provided to the neurons 1308*a*-1308*n* for analysis and connections between the known facts. The neurons 1308*a*-1308*n*, upon finding connections, provides the potential connections as outputs to the output layer 1312, which can determine a record match, no record match, or a probability of a record match.

In some embodiments, the neural network 1302 may be a convolutional neural network. The convolutional neural network can include an input layer, one or more hidden or intermediate layers, and an output layer. In a convolutional neural network, however, the output layer may include one fewer output neuron than the number of neurons in the intermediate layer(s), and each neuron may be connected to each output neuron. Additionally, each input neuron in the input layer may be connected to each neuron in the hidden or intermediate layer(s).

Such a neural network-based record matching system can be trained by operators, automatically self-trained the record matching system itself, or can be trained both by operators and by the record matching system itself to improve how records are or are not matched with each other. This can allow for the record matching system to improve the accuracy with which records are (or are not) matched with each other over time to reduce instances and likelihoods of overmatching or undermatching records.

For example, the record matching systems described and shown herein may determine which patient records belong to the same patient using one or more supervised machine-learning processes. These supervised machine-learning processes may include classification algorithms, defined as processes where the artificial neurons of the computer system derive, from training data, one or more sets of the matching rules described herein (e.g., one or more machine-learning models) for analyzing input records to determine whether two (or more) records match to the same person (or do not match to the same person).

The AI or machine-learning processes may be used to generate or update the machine-learning models used by the artificial neurons to compare information from the patient records. A machine-learning model can be or include a mathematical representation of a relationship between input records and outputs (e.g., indications of a match between records to the same person or indications of no match between records to the same person), as generated using the machine-learning processes described herein. An input is provided to one or more of the input neurons of the neural network 1302 after the model is created. The output neurons within the network 1302 generate an output based on the relationships that are derived or learned by the neurons in the intermediate or hidden layer(s) 1308. Connections between the nodes within each layer and/or between the layers 1304, 1308, 1312 and/or the neurons may be created via the process of training the record matching network or record matching system. This training can adjust connections, values of parameters, weights, etc., between the neurons in the layers 1304, 1308, 1312 of the neural network 1302 to reduce instances of overmatching or undermatching records over time (and relative to another system that does not change the connections, parameter values, weights, etc.). Additionally or alternatively, the record matching system can train itself by adding or creating rules or criteria for analyzing records for matches. This repeated training process can be referred to as deep learning.

This training can involve, for example, providing data as input to the neurons in the input layer 1304 of the record matching system (e.g., patient records), and having the neurons in the input layer 1304 and/or intermediate layer(s) 1308 of the record matching system apply the matching rules, criteria, and/or processes described herein. This application of the rules, criteria, and/or processes is performed by the neurons in the intermediate layer(s) 1308 to determine (e.g., as output from the output neurons in the output layer 1312) whether two or more of the records (in the provided data) match to the same patient (or do not match to the same patient). This output (e.g., identifications of records matching or not matching to the same person) can then be examined to determine whether the output is correct or not (e.g., determining whether the records actually match to the same person, or determining whether the analysis by the system was incorrect). This analysis and decision can be performed by one or more of the neurons in the layers 1304, 1308, 1312 of the neural network 1302, or can be manually performed (e.g., as a check on operation of the neural network 1302).

For erroneous matches or non-matches that are output by the record matching system, the matching rules, criteria, and/or processes used by one or more of the neurons in the record matching system can then be modified, augmented, or reduced. The rules or criteria can be modified by changing values of parameters or weights (as described herein), may be augmented by adding one or more rules or criteria that were not previously used to examine the records, and/or may be reduced by eliminating one or more rules or criteria that were previously used to examine the records. The same and/or different data (e.g., patient records) can subsequently be input into the input neurons in the input layer 1304, and the process repeated. For example, the output of the neurons in the output layer 1312 after the modification can be examined to determine whether the identified matches or non-matches are correct, with the matching rules, criteria, and/or processes used by the neurons in the intermediate layer(s) 1308 potentially modified again. This process can be repeated several times to improve the accuracy by which the record matching system matches (or does not match) records to each other. For example, the output(s) provided by the output neurons in the output layer 1312 can be examined to determine whether any overmatching or undermatching occurred. If any overmatching or undermatching did occur, then the processes performed by one or more of the neurons in the intermediate layer(s) 1308 can be modified as described herein. The process can then be repeated to gradually reduce instances of overmatching and/or undermatching.

In contrast to some known artificial intelligence or machine learning systems that use supervised learning to train the systems or networks, one or more embodiments of the neural network 1312 of the record matching systems described herein may use unsupervised learning to train the systems. For example, actual patient records may be used as the production data that is input into the input neurons of the neural network 1302 for analysis and identification of matches by the neurons in the intermediate layer(s) 1308. These patient records may not be known to match (or not match) each other prior to inputting the records into the record matching system. Instead, the output from the neurons in the output layer 1312 record matching system can be examined to determine whether the system-matched records (or records that are not identified as matches to the same person) are correct matches of records, incorrect matches of records, or missed matching of records (e.g., where two or more records are associated with the same person, but the system does not identify the records as matching). Optionally, field experience may be used for direct machine learning. Healthcare providers may learn about individual undermatches and overmatches with records, and correct these records. In one embodiment, the matching system can use these manual corrections to learn and infer refinements to parameters and rules.

The analysis of the output can be performed by receiving output from the neuron(s) in the output layer 1312 indicating that two (or more) records match the same patient; examining the matched records to confirm or refute that the records do, in fact, belong to the same patient; and generating feedback based on this examination. For example, the matched records may be used to provide a medical decision, such as filling a prescription, making a medical diagnosis, etc. The same or another system (e.g., a pharmacy benefit manager device, a physician's office, a hospital records system, a clinical information system, etc.) can determine (based on additional analysis of the matched records) whether the matched records do, in fact, belong to the same person. Alternatively, these other systems can include one or more persons that manually inspect the matches records to determine whether the records do contain medical data of the same person or different persons.

If these other automated and/or manual systems determine that the records matched by the record matching system do not match the same person (e.g., the records belong to different persons), then feedback data can be generated and provided back to the record matching systems. For example, the feedback data can be provided as input to one or more of the neurons in the input layer 1304 of the network 1302. This feedback data can identify mis-matches in the records. For example, a mismatch can be identified a binary match or no-match indication, can be identified by a subset of the data within the records that was found to indicate the records do not belong to the same person, or the like.

The record matching system can then change (or have changed) one or more parts of the matching rules or criteria used by the neurons in the intermediate layer(s) 1308 to examine the records, as described above. Weights or other parameters of the matching rules or criteria used by these neurons may be modified to train the record matching system to not overmatch or undermatch the records going forward. For example, the names associated with each other or otherwise identified as nicknames of each other may be changed. A set of nicknames such as "Eleanor," "Elenora," and "Ellie" may be expanded to also include "Ella" responsive to records having these nicknames being undermatched. Conversely, a set of nicknames such as "Aaron," "Ronald," "Veronica," and "Ronnie" may be reduced to not include "Veronica" responsive to records having these nicknames being overmatched. Because nicknames can change over time, the record matching system can repeatedly learn based on the feedback data whether to expand or contract the names included in a set of nicknames to reduce overmatching and undermatching of records.

As another example, the spellings of names associated with each other may be changed. A set of differently spelled names such as Hailey, Haley, Haylee, Hayleigh, Hayley, and Haylie may be expanded to include spellings such as Hailee and Haleigh based on the feedback data indicating the overmatch or undermatching of records due to the different spellings of certain names changing over time. Because the spelling of some names can change over time, the record matching system can repeatedly learn based on the feedback data whether to expand or contract the names included in a set of different spelled names to reduce overmatching and undermatching of records.

The record matching system can change the number of instances where records show different names in the same household but that share a unique demographic marker in at least a certain threshold proportion of households and/or volume of households in which the names co-exist. For example, based on the feedback data indicating overmatching or undermatching of records, the record matching system can change the threshold proportion of households and/or volume of households to reduce overmatching and/or undermatching. If the proportion of instances where the records show the different names in the same household with the same demographic marker is no greater than the threshold that is changed based on the feedback, then the record matching system can determine that there is not enough confidence to determine that the different names are nicknames. But if the proportion and/or volume of instances where the records show the different names with the same demographic marker is greater than the threshold that has been changed due to the feedback, then the record matching system can determine that there is enough confidence to determine that the different names are nicknames. Over time, this learning process can improve identification of common nicknames to improve the accuracy by which the record matching system identifies when records match to the same person.

The record matching system can change which demographic markers are examined in the records to determine whether any likelihoods of affinity within a family unit exist based on the feedback that is provided. For example, the record matching system (e.g., the manager device or the overmatch exclusion module) can change which of the date of birth, social security number (or portion thereof), person number, or the like, is used to determine whether an affinity exists (in the analysis of whether different names in records represent the same person, as described above). This change may be based on the feedback indicating that use of one or more demographic markers is resulting in record overmatching or undermatching. The demographic marker(s) that are changed can be used in future analysis of production data to evaluate whether the changed demographic marker(s) results in fewer or greater instances of overmatching and undermatching. Feedback based on this future analysis also can be used to repeatedly improve the record matching by the system.

As another example, the designated character string length of the personal identifiers in the records (that is required to be found before matching the records) can be changed based on the feedback data. As described above, the household matching module can examine the personal identifiers stored in the records to evaluate whether the personal identifiers share at least this designated character string length. As the designated length increases, there is greater confidence or probability that the records are associated with the same household and/or match each other, but the risk of undermatching records may increase. Conversely, as the designated length shortens, there is less confidence or probability that the records are associated with the same household and/or match each other, but the risk of overmatching records may increase. The record matching system (e.g., the household matching module) can change the length of this designated string based on the feedback to reduce future overmatching and undermatching of records over time.

For example, the household matching module can change the eight-character length string used to examine personal identifiers in different records to a longer length responsive to the feedback data indicating overmatching of records or a shorter length responsive to the feedback data indicating undermatching of records. Optionally, the household matching module can change the required number of matching characters within the personal identifiers, regardless of whether the characters are in a continuous string. Increasing the required number of matching characters can result in fewer overmatches (but may increase the number of undermatches), while decreasing the required number of matching characters can result in greater overmatches (but may reduce the number of undermatches).

The record matching system may change the threshold or designated number of residents associated with the same address based on the feedback data to reduce instances of overmatching or undermatching records. For example, the household matching module can change how many persons are associated with the same address before the address is identified as a collective address, as described above. The designated number of residents for an address to be identified as a collective address may initially be 250 residents, but the record matching system may increase or decrease this number responsive to the feedback data indicating too many overmatches or undermatches of records. For example, the required number of residents may be increased responsive to the feedback data indicating overmatching of records associated with that address, while the required number of residents may be decreased responsive to the feedback data indicating undermatching of records. Over time, the required number of residents can change based on the feedback data to improve overmatching and undermatching of records.

As another example of changing the rules or criteria based on the feedback data, the record matching system (e.g., the overmatch exclusion module) can change the designated time period or designated chronologic range used to compare household-sharing records having different dates of birth. For example, if too many overmatches are occurring, the overmatch exclusion module can shorten this time period to less than one year. If too many undermatches are occurring, the overmatch exclusion module can lengthen this time period.

The overmatch exclusion module can change the list of known truncated versions of names based on the feedback data. For example, the list of known truncated versions of names can be augmented with more names responsive to the feedback data indicating undermatching of records due to the additional names not being included in the list. Conversely, the list of known truncated versions of names can be edited or shortened to remove names responsive to the feedback data indicating overmatching of records due to the removed names previously being included in the list.

Similarly, the overmatch exclusion module can change which initials of names are included in a list used to determine whether different versions of the same name are used in different records, as described above, based on the feedback data. As another example, the edit distances used to compare demographic information in records to determine whether the records match may be changed based on the feedback data to reduce the number of overmatches and/or undermatches over time (as well as adapt to changing popularities of various names).

In another example, the type or length of the designated affinity (e.g., the edit distance) can be changed based on the feedback data. As described above, demographic information from records can be compared to determine whether at least the designated affinity exists between the records. Responsive to overmatching or undermatching being identified in the feedback data, the record matching system can lengthen, shorten, or change the type of designated affinity required for matching records. This can reduce the overmatching or undermatching of records over time.

The record matching system may train itself or be trained based on the feedback data by adding and/or removing rules, criteria, or parameters. For example, during one analysis of records, the record matching system may use a first set of the rules, criteria, and/or parameters described herein. Based on feedback indicating that the record matching using this first set of rules, criteria, and/or parameters including overmatching or undermatching, the recording matching system may train itself (or be trained) by using a second set of rules, criteria, and/or parameters for future analysis of the same and/or different records. This second set may include one or more additional rules, criteria, and/or parameters that were not in the first set during at least one previous iteration of record analysis. Additionally or alternatively, second set may include one or more fewer rules, criteria, and/or parameters that were in the first set during at least one previous iteration of record analysis.

The record matching systems and methods described herein provide a technical improvement over conventional record matching techniques by significantly reducing the complexity of manually matching records with each other in a timely manner (e.g., in the time period where medical decisions need to be made based on the records, such as within several minutes but less than an hour). The complexity of matching the records can be reduced significantly because the only activity required from human users for record-matching purposes is to use the information from the records that are matched for making one or more medical decisions at a suitable timing or within a suitable time period for the patient. Compared to prior art and conventional record matching techniques, the subject matter described herein matches records in less time, with less user interaction, and with fewer errors.

One or more embodiments of the subject matter described herein involve a computer's utilization of a machine learning or statistical model to analyze many medical records received from multiple, different sources to determine which records match each other or include information for the same person, regardless of errors or mismatches between identifying demographic information that otherwise would result in the records being incorrectly matched to the same person or incorrectly matched to different persons, thereby posing significant and deadly risks to patients. While some examination of medical records can be performed mentally or with pen and paper, the subject matter described herein may transform (through training or machine learning) a neural network and data contained in the medical records to determine whether records match the same or different persons.

In one embodiment, an AI record matching system is provided that includes one or more processors at a healthcare management system. These processor(s) may obtain patient records having demographic information and may compare the demographic information in the patient records to determine that the demographic information in the patient records do not match. Responsive to this determination, the processors may determine whether the non-matching demographic information in the patient records are linked with a common household. The processor(s) can make this determination by comparing the patient records using a first set of one or more rules, criteria, or parameters.

This comparing may be performed by determining (a) whether the demographic information in the patient records that do not match include a common first name and a same date of birth and whether the patient records indicate membership in a common health care plan, (b) whether the demographic information in the patient records that do not match include personal identifiers that share at least a designated length of a character string, (c) whether the demographic information in the patient records that do not match include a common street address name, a common postal code, and the common first name and include a combination of a street address number and the common street address name is used by no more than a designated number of people, and/or (d) whether the demographic information in the patient records that do not match include the common street address name, the street address number, and the common postal code, and the combination of the street address number and the common street address name is used by no more than the designated number of people.

The processor(s) may determine whether the non-matching demographic information in the patient records includes exclusionary intra-family overmatching data according to the first set of rules, criteria, and/or parameters responsive to determining that the non-matching demographic information are linked to with the common household. The processors may determine whether the demographic information includes the exclusionary intra-family overmatching data by determining (e) whether the demographic information in the patient records that do not match include the common first name but different dates of birth that are within a designated time period of each other, (f) whether the demographic information in the patient records that do not match includes the same date of birth but different first names that include a designated nickname, a truncated variation of the first names, or initials of the first names, (g) whether the demographic information in the patient records that do not match include different character strings that have at least a designated length of identical characters, and/or (h) whether the demographic information in the patient records that do not match includes the different first names that differ by no more than a designated edit distance.

The processors may determine that the patient records include the medical information of the same person responsive to determining that the non-matching demographic information in the patient records are linked with the common household but do not include the exclusionary intra-family overmatching data or responsive to determining that the patient records do not all include the medical information of the same person responsive to determining that the demographic information in the patient records are not linked with the common household or include the exclusionary intra-family overmatching data. The processors may repeatedly receive feedback data indicative of overmatching and/or undermatching the patient records to each other using the first set of rules, criteria, and/or parameters.

The processors may be repeatedly trained based on the feedback data by repeatedly modifying the rules, criteria, and/or parameters of the first set into a modified set that differs from the first set. The processors may use the modified rules, criteria, and/or parameters in the second set during repeated training of the processors to reduce the overmatching and/or undermatching of the patient records during successive iterations of the one or more processors examining the patient records.

For example, the processors may perform the operations of comparing records, determining whether the records match or do not match the same person (e.g., include information about the same patient), and outputting indication of the match (or not matching) of the records to the same person. Depending on whether the processors are correct or not, the feedback data is provided to the processors and the rules, criteria, and/or parameters used to compare the records are changed. The processors can then repeat these steps for the same or different records. For example, the processors can repeat comparing the records using the modified rules, criteria, and/or parameters, determining whether the records match or don't match, providing output indicating the match or lack of match, receiving feedback based on the output, and changing the rules, criteria, and/or parameters for future comparison of the same or different records.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, present disclosure may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, demonstrates the flow of information (such as data or instructions) that is of interest to the illustration. For example, when element A and element B exchange a variety of information, but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, present disclosure may lie in less than all features of a single disclosed embodiment. Thus, the following claims are hereby incorporated into the Detailed Description, with each claim standing on its own as a separate embodiment.

What is claimed is:

1. An artificial intelligence (AI) record matching system comprising:
   one or more processors at a healthcare management system that are configured to obtain patient records having demographic information, the one or more processors configured to compare the demographic information in the patient records and determine that the demographic information in the patient records does not match,
   responsive to determining that the demographic information in the patient records does not match, the one or more processors are configured to:
      determine whether the demographic information in the patient records that do not match are linked with a common household by comparing the patient records using artificial neurons connected with each other in different layers,
      compare a first model containing a first set of one or more rules, criteria, or parameters that include mathematical relationships between (a) the patient records that are input to the artificial neurons and (b) outputs from the artificial neurons that indicate whether the patient records match or do not match each other, the mathematical relationships including one or more of a limit on an edit distance on differences between the demographic information in the patient records, a value for a likelihood of affinity measurement between the demographic information in the patient records, or a threshold number or threshold percentage of times that the demographic information in the patient records match,
      compare the records using the first set of the one or more rules, criteria, or parameters to determine:
         (c) whether the demographic information in the patient records that do not match include a common first name and a same date of birth and whether the patient records indicate membership in a common health benefit plan,
         (d) whether the demographic information in the patient records that do not match include personal identifiers that share at least a designated length of a character string,
         (e) whether the demographic information in the patient records that do not match include a common street address name, a common postal code, and the common first name and include a combination of a street address number and the common street address name is used by no more than a designated number of people, or
         (f) whether the demographic information in the patient records that do not match include the common street address name, the street address number, and the common postal code, and the combination of the street address number and the common street address name is used by no more than the designated number of people,
      determine whether the demographic information in the patient records that do not match includes exclusionary intra-family overmatching data according to the first set of one or more rules, criteria, or parameters and using the artificial neurons responsive to determining that the demographic information in the patient records that do not match are linked to with the common household,
      determine whether the demographic information includes the exclusionary intra-family overmatching data by using the artificial neurons to determine:
         (g) whether the demographic information in the patient records that do not match include the common first name but different dates of birth that are within a designated time period of each other,
         (h) whether the demographic information in the patient records that do not match includes the same date of birth but different first names that include a designated nickname, a truncated variation of the first names, or initials of the first names,
         (i) whether the demographic information in the patient records that do not match include different character strings that have at least a designated length of identical characters, or
         (j) whether the demographic information in the patient records that do not match includes the different first names that differ by no more than a designated edit distance,
      determine that the patient records include medical information of a same person using the artificial neurons and responsive to:
         determining that the demographic information in the patient records that do not match are linked with the common household but do not include the exclusionary intra-family overmatching data or
         determining that the patient records do not all include the medical information of the same person responsive to determining that the demographic information in the patient records are not linked with the common household or include the exclusionary intra-family overmatching data, repeatedly receive feedback data indicative of one or more of overmatching or undermatching the patient records to each other using the first set of one or more rules, criteria, or parameters, and repeatedly train the artificial neurons based on the feedback data by repeatedly modifying the one or more rules, criteria, or parameters of the first set to change connections between the artificial neurons in the different layers into a modified second set of the one or more rules, criteria, or parameters that differs from the first set, the one or more processors configured to use the one or more rules, criteria, or parameters that are modified in the second set during repeated training of the connections between the artificial neurons to reduce the one or more of overmatching or undermatching of the patient records during successive iterations of the one or more processors examining the patient records.

2. The AI record matching system of claim 1, wherein the one or more processors are configured to use the modified set of the one or more rules, criteria, or parameters as the first set of the one or more rules, criteria, or parameters during at least one of the successive iterations of the one or more processors examining the patient records, the one or more processors configured to be repeated re-trained by using the feedback data obtained following using the modified set of the one or more rules, criteria, or parameters as the first set of the one or more rules, criteria, or parameters and modifying the first set of the one or more rules, criteria, or parameters into another iteration of the modified set of the one or more rules, criteria, or parameters.

3. The AI record matching system of claim 1, wherein the one or more processors are configured to create a database that organizes different portions of the demographic information of at least one of the records in the database, the database created by the one or more processors to include connecting data elements that each include a name and a value that indicate the patient records that match the same person, the database created by the one or more processors to indicate that the patient records that match include medical data of the same person without changing the demographic information in the patient records, the one or more processors configured to use the database that is created and the modified set of the one or more rules, criteria, or parameters during the successive iterations of examination of the patient records to determine that the patient records match the same person without repeating determining whether the demographic information in the patient records are linked with the common household and without repeating determining whether the demographic information in the patient records include the exclusionary intra-family overmatching data.

4. The AI record matching system of claim 1, wherein the one or more processors are configured to determine whether the patient records are linked with the common household includes by identifying a first combination of the first name and the date of birth in the patient records, identifying a second combination of the first name and the date of birth in the patient records, determining whether the first combination is associated with a first address in the patient records, and determining whether the second combination is associated with a second address in the patient records.

5. The AI record matching system of claim 4, wherein the first combination and the second combination both include the first name and the date of birth of a third person.

6. The AI record matching system of claim 1, wherein the one or more processors also are configured to create a complete patient history by combining a clinical histories associated with the patient records that are determined to include the medical information of the same person, the one or more processors also configured to make one or more automated clinical decisions using the complete patient history and to enable clinicians to make one or more manual decisions using the complete patient history.

7. The AI record matching system of claim 1, wherein the one or more processors are configured to obtain the patient records from different data sources.

8. The AI record matching system of claim 1, wherein the one or more processors are configured to obtain the patient records from a same data source.

9. The AI record matching system of claim 1, wherein the one or more processors are configured to modify at least one of the patient records by adding or changing one or more of data included in a first patient record of the patient records to match data included in a second patient record of the patient records, or the first patient record to match the second patient record.

10. The AI record matching system of claim 1, wherein the one or more processors are configured to determine that a first record and a second record of the patient records have the demographic information that does not match but that include the medical information of the same person responsive to the first record being associated with continuing treatment of the same person and the second record not being associated with the continuing treatment of the same person.

11. The AI record matching system of claim 1, wherein the exclusionary intra-family overmatching data include one or more of common health benefit plan membership numbers that differ by more than a designated amount, or genders.

12. The AI record matching system of claim 1, wherein the one or more processors are configured to determine that the demographic information of the patient records include the exclusionary intra-family overmatching data responsive to both the demographic information being associated with a designated type of the common health benefit plan.

13. The AI record matching system of claim 1, wherein the one or more processors are configured to determine that the first and second demographic information include the exclusionary intra-family overmatching data responsive to using matching rules associated with a designated type of health benefit that are used to determine whether the demographic information in the patient records are not associated with the same person.

14. The AI record matching system of claim 13, wherein the matching rules are less stringent for determining that mismatched data in the demographic information are associated with the same person for one or more first designated types of health benefits than for one or more second designated types of health benefits.

15. The AI record matching system of claim 1, wherein the one or more processors are configured to obtain the patient records from one or more databases that separately store the patient records with separate identification numbers or separate last names, and the one or more processors are configured to cite on individual rows in the one or more databases with possible connections between the patient records so that each of several identifiers in the patient records can be examined for joining with each other according to a separation connection criterium associated with the corresponding identifier.

16. The AI record matching system of claim 1, wherein the one or more processors are configured to determine the demographic information to be associated with the same person regardless of a typographic error in the demographic information.

17. The AI record matching system of claim 16, wherein the typographic error is one or more of a transposition error, a designated portion of a character string in the demographic information, or one or more additional characters in one or more of a prefix or a suffix in the demographic information.

18. The AI record matching system of claim 1, wherein the one or more processors are configured to identify a drug contraindication or other treatment contraindication responsive to determining that the patient records are associated with the same person, the one or more processors configured to communicate an alert to one or more of a medication provider or a healthcare provider to stop prescription, administration, or delivery of a drug or other health care treatment based on the drug contraindication or the other treatment contraindication that is identified.

19. A method comprising:
examining patient records using artificial neurons arranged in different layers in an artificial intelligence (AI) record matching system, the artificial neurons connected with each other and configured to compare the patient records using a model having one or more rules, criteria, or parameters that include connections of mathematical relationships between (a) the patient records that are input to the artificial neurons and (b) outputs from the artificial neurons that indicate whether the patient records match or do not match each other, the mathematical relationships including one or more of a limit on an edit distance on differences between demographic information in the patient records, a value for a likelihood of affinity measurement between the demographic information in the patient records, or a threshold number or threshold percentage of times that the demographic information in the patient records match;
determining whether any of the patient records include different demographic information but include same medical information for a same person based on comparing the patient records using the one or more rules, criteria, or parameters;
determining whether the demographic information in the patient records that do not match include a common first name and a same date of birth;
determining whether the patient records indicate membership in a common health care plan;
determining, for the patient records that do not match, whether the demographic information includes exclusionary intra-family overmatching data according to the one or more rules, criteria, or parameters by determining whether the demographic information in the patient records that do not match includes the same date of birth but different first names that include a designated nickname, a truncated variation of the first names, or initials of the first names;
receiving feedback data indicating an overmatching of the patient records to the same person or an undermatching of the patient records to the same person;
training the AI record matching system by modifying the connections between the artificial neurons based on the feedback data; and
iteratively repeating one or more of examining the patient records, determining whether any of the patient records include the different demographic information but the same medical information for the same person, receiving the feedback data, and training the AI record matching system to reduce one or more of the overmatching or the undermatching of the patient records during successive iterations of examining the patient records.

20. An artificial intelligence (AI) record matching system comprising:
one or more processors configured to:
compare patient records using a model having one or more rules, criteria, or parameters that connect artificial neurons in different layers of the AI record matching system and that include connections of mathematical relationships between (a) the patient records that are input to the artificial neurons and (b) outputs from the artificial neurons that indicate whether the patient records match or do not match each other, the mathematical relationships including one or more of a limit on an edit distance on differences between demographic information in the patient records, a value for a likelihood of affinity measurement between the demographic information in the patient records, or a threshold number or threshold percentage of times that the demographic information in the patient records match,
determine whether any of the patient records include different demographic information but include same medical information for a same person based on comparing the patient records using the one or more rules, criteria, or parameters,
determine whether the demographic information in the patient records that do not match include a common first name and a same date of birth and whether the patient records indicate membership in a common health care plan,
determine, for the patient records that do not match, whether the demographic information includes exclusionary intra-family overmatching data according to the one or more rules, criteria, or parameters by determining whether the demographic information in the patient records that do not match includes the same date of birth but different first names that include a designated nickname, a truncated variation of the first names, or initials of the first names,
receive feedback data indicating an overmatching of the patient records to the same person or an undermatching of the patient records to the same person,
train the artificial neurons to change connections between the artificial neurons by modifying the one or more rules, criteria, or parameters based on the feedback data, and
iteratively repeat one or more of examining the patient records using the artificial neurons, determining whether any of the patient records include the different demographic information but the same medical information for the same person using the artificial neurons, receiving the feedback data, and training the connections between the artificial neurons to reduce one or more of the overmatching or the undermatching of the patient records during successive iterations of examining the patient records.

* * * * *

UNITED STATES PATENT AND TRADEMARK OFFICE
CERTIFICATE OF CORRECTION

| | |
|---|---|
| PATENT NO. | : 11,515,018 B2 |
| APPLICATION NO. | : 17/682352 |
| DATED | : November 29, 2022 |
| INVENTOR(S) | : Howard M. Sragow et al. |

It is certified that error appears in the above-identified patent and that said Letters Patent is hereby corrected as shown below:

In the Claims

In Claim 13, Column 64, Line 48, delete "first and second"

Signed and Sealed this
Seventh Day of March, 2023

*Katherine Kelly Vidal*

Katherine Kelly Vidal
*Director of the United States Patent and Trademark Office*